United States Patent
Shibata et al.

(10) Patent No.: US 12,398,095 B2
(45) Date of Patent: Aug. 26, 2025

(54) PHOTORESPONSIVE COMPOUND, ADHESIVE, SWITCHING MATERIAL, AND TONER CONTAINING THE PHOTORESPONSIVE COMPOUND, AND IMAGE FORMING METHOD USING THE TONER

(71) Applicant: Konica Minolta, Inc., Tokyo (JP)

(72) Inventors: Toyoko Shibata, Tokyo (JP); Haruo Horiguchi, Koganei (JP); Yukiko Nakai, Toyohashi (JP); Kouji Sugama, Musashino (JP); Kazuaki Nakamura, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 885 days.

(21) Appl. No.: 17/406,045

(22) Filed: Aug. 18, 2021

(65) Prior Publication Data
US 2022/0064107 A1   Mar. 3, 2022

(30) Foreign Application Priority Data

Aug. 28, 2020   (JP) .................................. 2020-145011

(51) Int. Cl.
*G03G 9/097* (2006.01)
*C07C 251/16* (2006.01)
(Continued)

(52) U.S. Cl.
CPC ........ *C07C 251/16* (2013.01); *C07D 207/335* (2013.01); *C07D 207/34* (2013.01);
(Continued)

(58) Field of Classification Search
CPC .............................. G03G 9/091; G03G 9/0924
See application file for complete search history.

(56) References Cited

U.S. PATENT DOCUMENTS

| 3,597,211 A | 8/1971 | Betts et al. |
| 2007/0127329 A1* | 6/2007 | Erben ................. G11B 7/24044 |

(Continued)

FOREIGN PATENT DOCUMENTS

| JP | 09-043879 | * | 2/1997 | ............... G03G 5/06 |
| JP | 2000-305294 | * | 11/2000 | ............... G03G 5/06 |

(Continued)

OTHER PUBLICATIONS

Translation of abstract of JP 2000-305294.*
(Continued)

*Primary Examiner* — Peter L Vajda
(74) *Attorney, Agent, or Firm* — LUCAS & MERCANTI, LLP

(57) ABSTRACT

A compound that is fluidized by light irradiation and reversibly non-fluidized and is represented by the following general formula (1):

[Chemical Formula 1]

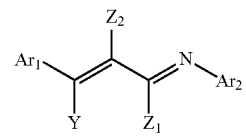

General formula (1)

In the general formula (1),
Ar$_1$ and Ar$_2$ each independently represent an aromatic hydrocarbon group optionally having a substituent or an aromatic heterocyclic group optionally having a substituent, and (Continued)

Y, $Z_1$, and $Z_2$ each independently represent a hydrogen atom or a lower alkyl group.

14 Claims, 2 Drawing Sheets

(51) Int. Cl.
| | |
|---|---|
| *C07D 207/335* | (2006.01) |
| *C07D 207/34* | (2006.01) |
| *C07D 209/14* | (2006.01) |
| *C07D 213/74* | (2006.01) |
| *C07D 307/52* | (2006.01) |
| *C07D 307/66* | (2006.01) |
| *C07D 333/22* | (2006.01) |
| *C07D 333/36* | (2006.01) |
| *C09J 9/00* | (2006.01) |
| *C09J 11/06* | (2006.01) |
| *G03G 15/20* | (2006.01) |

(52) U.S. Cl.
CPC ......... *C07D 209/14* (2013.01); *C07D 213/74* (2013.01); *C07D 307/52* (2013.01); *C07D 307/66* (2013.01); *C07D 333/22* (2013.01); *C07D 333/36* (2013.01); *C09J 9/00* (2013.01); *C09J 11/06* (2013.01); *G03G 9/09775* (2013.01); *G03G 15/2007* (2013.01); *C09J 2301/304* (2020.08); *C09J 2301/408* (2020.08)

(56) References Cited

U.S. PATENT DOCUMENTS

2011/0196174 A1    8/2011    Bennett
2013/0066068 A1    3/2013    Norikane et al.

FOREIGN PATENT DOCUMENTS

| JP | 2003301121 A | 10/2003 |
| JP | 2011-256155 A | 12/2011 |
| JP | 2014-191078 A | 10/2014 |

OTHER PUBLICATIONS

Translation of JP 2000-305294.*
Bayle, J.P. & Fung, B.M., "Nematic Compounds Containing a Four-Unit Linking Group and the Order Parameters of the Mesogenic Core," New Journal of Chemistry, 1993, 17(5), 345-349.*
Notice of Reasons for Refusal dated Sep. 24, 2024, issued for the corresponding Japanese Patent Application No. 2020-145011, 10 pages, with English translation.
Hua, G., et al.: "Reactivity of Woollins' Reagent toward 2-En-1-imines (Schiff Bases): A Facile Approach to Synthesize New Selenium-Phosphorus-Nitrogen Heterocycles", European Journal of Inorganic Chemistry, Oct. 21, 2019, pp. 4682-4689, No. 43.
Fallon, B.J., et al.: "Synthesis of 1,2-Dihydropyridines Catalyzed by Well-Defined Low-Valent Cobalt Complexes: C—H Activation Made Simple", ACS Catalysis, Nov. 19, 2015, pp. 7493-7497, vol. 5, No. 12.
Al-Rawi, J. & Saleem, L.M: "The Studies of 13C NMR Chemical Shifts and Induced Lanthanide Shift Reagent Cis-trans Isomerization of N-Cinamylidene-hexyl, t-butyl and Substituted Aryl-Aminess", Spectroscopy Letters , 1991 , 24(1), 161-171.
Saleem, L.M. & Authman A.S.: "1H NMR Study of the Photoisomerization of Cinamylidene-2-Methyl-5-Chloro aniline", Spectroscopy Letters , 1992 , 25(6) , 799-809.

* cited by examiner

PHOTORESPONSIVE COMPOUND, ADHESIVE, SWITCHING MATERIAL, AND TONER CONTAINING THE PHOTORESPONSIVE COMPOUND, AND IMAGE FORMING METHOD USING THE TONER

TECHNOLOGICAL FIELD

The present invention relates to a photoresponsive compound, an adhesive, a switching material, and a toner containing the photoresponsive compound, and an image forming method using the toner.

BACKGROUND

Along with the development of energy saving measures and media compatible with energy saving, systems for fixing a toner with energy other than heat have attracted attention. In particular, fixing a toner by light has attracted attention, and a developer softened by light (light-melting toner) has also been reported.

The azobenzene compounds used in JP 2011-256155 A (corresponding to US 2013/0066068 A) and JP 2014-191078 A are compounds well known as an optical phase transition material that absorbs light and undergoes phase transition from a solid to a liquid. The optical phase transition of the azobenzene compounds is considered to be caused by disorder of the crystal structure due to trans-cis isomerization.

SUMMARY

Unfortunately, the azobenzene compounds described in JP 2011-256155 A (corresponding to US 2013/0066068 A) and JP 2014-191078 A have strong absorption due to n-π* transition in a long wavelength region, and exhibit an orange color. The orange color produces a problem since it affects color reproducibility when the azobenzene compound is used in a color material of a toner or the like.

In addition, toners containing the azobenzene compounds described in JP 2011-256155 A (corresponding to US 2013/0066068 A) and JP 2014-191078 A have a problem in color reproducibility as a toner, since the azobenzene compounds have an orange color. Further, a toner that is fixed by an external stimulus other than heat fixing has a problem of low productivity because the toner is insufficient in the softening rate required for fixing.

Meanwhile, according to the studies made by the present inventors, it was found that an azomethine compound having a structure in which benzene rings are connected by an azomethine group has a problem that even when the azomethine compound is changed from a trans isomer to a cis isomer by light irradiation, a toner containing the azomethine compound is insufficient in maintaining a softened state necessary for fixing due to a reverse reaction that is too fast.

Therefore, objects of the present invention are to provide a compound that is fluidized by light irradiation and reversibly non-fluidized and is not significantly colored, an adhesive, a switching material, and a toner containing the compound, and an image forming method using the toner.

The present inventors have intensively studied in view of the above-mentioned problems. As a result, the present inventors have found that the above-mentioned problems are solved by the following compound, and have completed the present invention.

To achieve at least one of the abovementioned objects, according to an aspect of the present invention, a compound that is fluidized by light irradiation and reversibly non-fluidized and is represented by the following general formula (1) is provided:

[Chemical Formula 1]

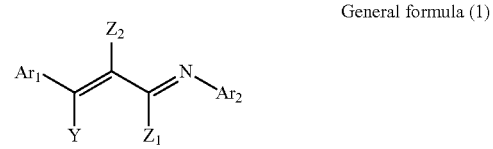

General formula (1)

In the general formula (1), $Ar_1$ and $Ar_2$ each independently represent an aromatic hydrocarbon group optionally having a substituent (a) or an aromatic heterocyclic group optionally having a substituent (b), and $Y$, $Z_1$, and $Z_2$ each independently represent a hydrogen atom or a lower alkyl group.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

In FIG. 1, reference sign 1 represents a photoreceptor, reference sign 2 represents a charger, reference sign 3 represents an exposure device, reference sign 4 represents a developing unit, reference sign 5 represents a transfer unit, reference sign 6 represents a static elimination unit, reference sign 7 represents a sheet conveying system, reference sign 8 represents a cleaning unit, reference sign 9 represents a pressure-bonding unit, reference sign 10 represents an image forming unit, reference sign 11 represents a sheet feeder, reference sign 12 represents a conveying roller, reference sign 13 represents a conveying belt, reference sign 14 represents a sheet ejector, reference sign 15 represents a manual sheet feeder, reference sign 16 represents a tray, reference sign 17 represents a thermo-hygrometer, reference sign 20 represents an image processing unit, reference sign 24 represents a sheet reversing unit, reference sign 40 represents an irradiation unit, reference sign 50 represents a transfer roller, reference sign 71 represents an image reading device, reference sign 72 represents an automatic document feeder, reference sign 85 represents a blade, reference sign 90 represents a control unit, reference signs 91 and 92 represent pressurizing members, reference sign 100 represents an image forming apparatus, reference sign d represents a document, and reference sign S represents a recording sheet.

In FIG. 2, reference sign 1 represents a photoreceptor, reference sign 2 represents a charger, reference sign 3 represents an exposure device, reference sign 4 represents a developing unit, reference sign 5 represents a transfer unit, reference sign 8 represents a cleaning unit, reference sign 9 represents a pressure-bonding unit, reference sign 10 represents an image forming unit, reference sign 13 represents a conveying belt, reference sign 40 represents an irradiation unit, reference sign 85 represents a blade, and reference signs 91 and 92 represent pressurizing members.

DETAILED DESCRIPTION OF EMBODIMENTS

Figure 1:
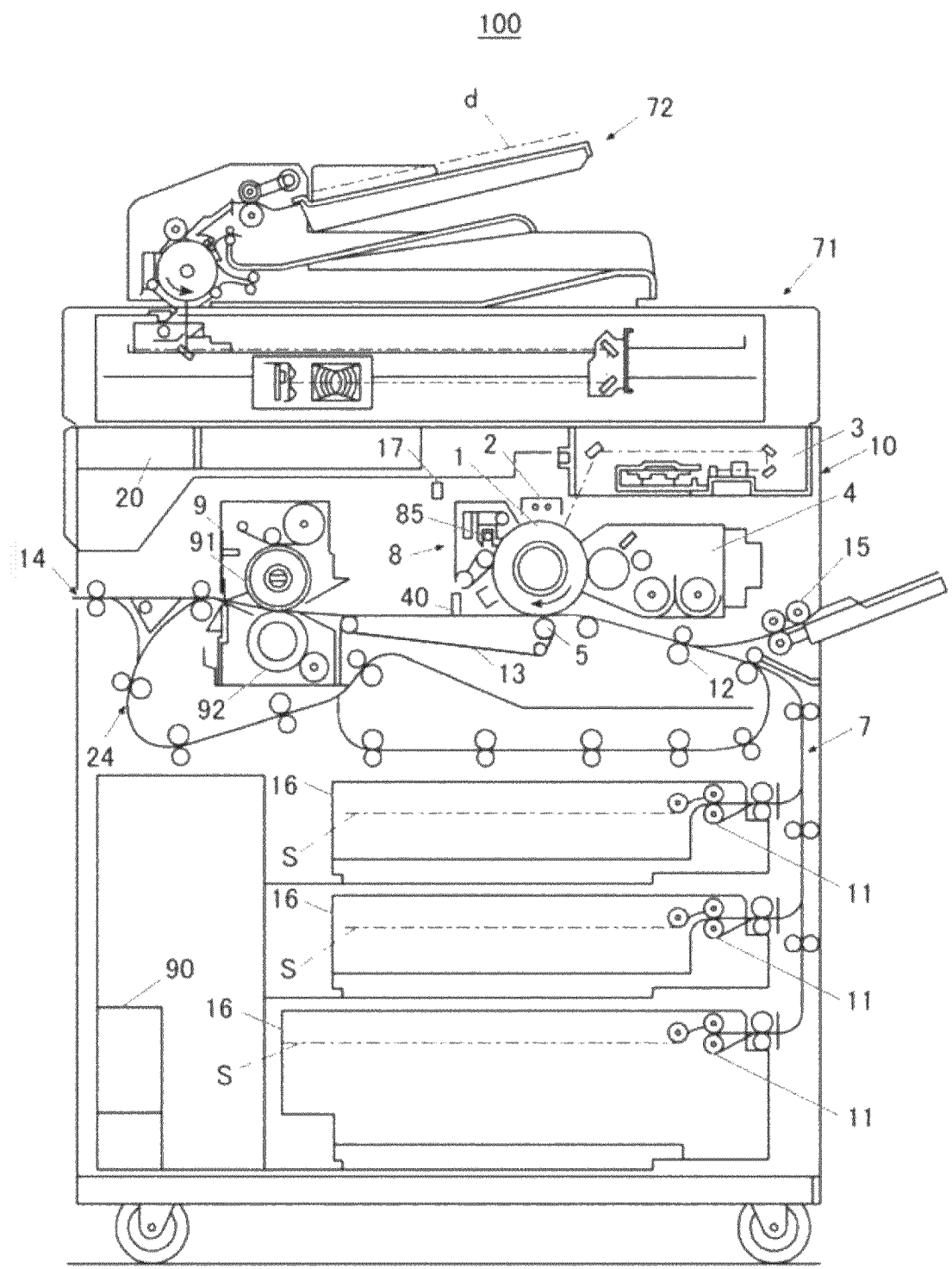
FIG. 1 is a schematic cross-sectional view illustrating an image forming apparatus used in an image forming method according to an embodiment of the present invention.

Hereinafter, one or more embodiments of the present invention will be described with reference to the drawings. However, the scope of the invention is not limited to the disclosed embodiments.

A compound according to an embodiment of the present invention is a compound that is fluidized by light irradiation and reversibly non-fluidized and is represented by the following general formula (1).

[Chemical Formula 2]

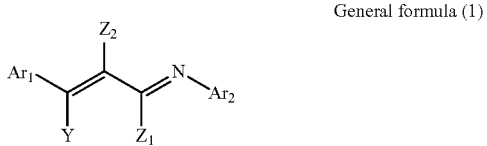

General formula (1)

In the general formula (1), $Ar_1$ and $Ar_2$ each independently represent an aromatic hydrocarbon group optionally having a substituent (a) or an aromatic heterocyclic group optionally having a substituent (b), and Y, $Z_1$, and $Z_2$ each independently represent a hydrogen atom or a lower alkyl group.

A propenimine compound represented by the general formula (1) is fluidized by light irradiation and reversibly non-fluidized, and does not affect desired color reproduction when being mixed with a colorant in application to a toner. As a result, the softening rate of the toner by light irradiation is remarkably improved, and the softened state necessary for fixing is maintained, so that image fixability is improved.

The reason why the compound of the present invention and the toner containing the compound produce the above-mentioned effect is not clear in detail, but the effect is possibly produced by the following mechanism. Note that the following mechanism is based on speculation, and the present invention is not limited to the following mechanism at all. In the following description, the compound represented by the general formula (1) is also simply referred to as a "propenimine compound".

The azobenzene compounds described in JP 2011-256155 A (corresponding to US 2013/0066068 A) and JP 2014-191078 A have strong absorption due to n-π* transition in a long wavelength region, and hardly achieve desired color reproduction when being mixed with a colorant at the time of addition to a toner. In contrast, the propenimine compound of the present invention is capable of weakening the strong absorption due to n-π* transition present in a long wavelength region, and thus can achieve desired color reproduction when being mixed with a colorant.

In addition, in the compound that is reversibly fluidized and non-fluidized associated with photoisomerization, it is considered that when a non-fluid trans isomer (E) is irradiated with light and isomerized to a cis isomer (Z), an ordered structure of the compound is disordered and a phase transition change, that is, a fluidization phenomenon can be induced. It is also considered that when the cis isomer (Z) returns to the trans isomer (E), an ordered structure is formed again, and a non-fluidization phenomenon can be induced.

Therefore, in order to induce the phenomenon that the compound is fluidized by light irradiation and reversibly non-fluidized, it is considered necessary that many trans isomers (E) be isomerized to cis isomers (Z) at the time of fluidization. Unfortunately, it is known that an azomethine compound generally has a higher rate of a Z→E reaction (non-fluidization reaction), which is a reverse reaction, than an azobenzene compound does, and according to the studies made by the present inventors, it is expected that an azomethine compound having benzene rings introduced at both ends thereof is disadvantageous for inducing a phenomenon that the compound is fluidized by light irradiation and reversibly non-fluidized. In addition, the fact that the rate of the Z→E reaction is high is considered to mean that the energy barrier in the Z→E reaction is low, and therefore the compound quickly returns to the trans isomer (E).

Therefore, the present inventors have considered that the rate of the Z→E reaction can be controlled by controlling the energy barrier in the Z→E reaction, and have succeeded in controlling the rate of the Z→E reaction by introducing a vinylene group having a high energy barrier and a low rate of the Z→E reaction to an azomethine group having a low energy barrier.

In addition, similarly to the case of the azobenzene compound described above, the optical phase transition of the azomethine compound is considered to be caused by disorder of the crystal structure due to trans-cis isomerization. In general, the optical phase transition of the azomethine compound occurs only at the outermost surface of the crystal structure, since the azomethine compound has a strong π-π interaction between molecules. Meanwhile, in the propenimine compound of the present invention, aromatic rings are each substituted with an alkyl group or an alkoxy group. As a result, the propenimine compound of the present invention forms a specific crystal structure in which, in a periodic structure dominated by the π-π interaction, a structure isotropically disturbed by thermal motion of an alkyl group or an alkoxy group coexists. Therefore, when the cis-trans isomerization reaction locally proceeds and the π-π interaction of the propenimine moiety is reduced, isotropic melting occurs in a chain manner in the entire system. Therefore, it is considered that in the compound of the present invention, trans-cis isomerization is more likely to proceed, and fluidization is more likely to occur.

For these reasons, it is considered that the propenimine compound of the present invention can induce a phenomenon that the compound is fluidized and reversibly non-fluidized associated with photoisomerization while being colorless. Moreover, addition of the compound of the present invention to a toner can realize a toner that can be fixed by light irradiation and has high color reproducibility, and an image forming method using the toner. Further, irradiation of the propenimine compound of the present invention with light to isomerize the compound can induce reversible fluidization and non-fluidization phenomena, and the compound can also be used as an adhesive and an optical switching material.

In the present specification, the term "fluidized" refers to a state in which deformation occurs without external force or with small external force.

Hereinafter, an embodiment of the present invention will be described. However, the scope of the present invention is not limited to the disclosed embodiment.

In the present specification, the "from X to Y" indicating the range means "X or more and Y or less". In the present specification, unless otherwise specified, operations and measurements of physical properties and the like are performed under conditions of room temperature (20° C. or more and 25° C. or less)/a relative humidity of 40% RH or more and 50% RH or less.

<Propenimine Compound>

The propenimine compound of the present invention is a compound represented by the following general formula (1). As described in the above-mentioned mechanism, the propenimine compound of the present invention can induce a phenomenon that the compound is fluidized and reversibly non-fluidized associated with photoisomerization while being colorless, and addition of the compound to a toner provides a toner that can be fixed by light irradiation and has high color reproducibility.

[Chemical Formula 3]

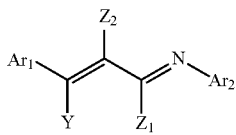

General formula (1)

In the general formula (1), $Ar_1$ and $Ar_2$ each independently represent an aromatic hydrocarbon group optionally having a substituent (a) or an aromatic heterocyclic group optionally having a substituent (b). The aromatic hydrocarbon group is a residue resulting from removal of hydrogen from an aromatic hydrocarbon. The number of carbon atoms of the aromatic hydrocarbon group is preferably 6 or more and 30 or less, and more preferably 6 or more and 20 or less from the viewpoint of exhibiting aromaticity and effectively exhibiting the effects of the invention. The aromatic heterocyclic group is a monocyclic or polycyclic (condensed) heterocyclic group that exhibits aromaticity and contains, as constituent atoms of the ring, a heteroatom in addition to a carbon atom. Examples of the heteroatom include an oxygen atom, a sulfur atom, a nitrogen atom, a phosphorus atom, a boron atom, an antimony atom, an arsenic atom, a bismuth atom, a selenium atom, a silicon atom, a tellurium atom, a tin atom, and a germanium atom. From the viewpoint of exhibiting aromaticity and effectively exhibiting the effects of the invention, the heteroatom is preferably an oxygen atom, a sulfur atom, or a nitrogen atom. The number of the heteroatoms is required to be 1 or more, and is preferably 1 or more and 3 or less from the viewpoint of exhibiting the effects of the invention more effectively.

The aromatic hydrocarbon group and the aromatic heterocyclic group (also collectively and simply referred to as "aromatic ring groups") are not particularly limited, and specific examples thereof include a benzene ring group, a naphthalene ring group, a thiophene ring group, a furan ring group, a pyrrole ring group, a pyrazole ring group, an imidazole ring group, and a thiazole ring group.

More specifically, examples of the aromatic hydrocarbon group include a benzene ring group (phenyl group), a biphenyl ring group, a naphthalene ring group, an azulene ring group, an anthracene ring group, a phenanthrene ring group, a pyrene ring group, a chrysene ring group, a naphthacene ring group, a triphenylene ring group, an o-terphenyl ring group, an m-terphenyl ring group, a p-terphenyl ring group, an acenaphthene ring group, a coronene ring group, a fluorene ring group, a fluoranthene ring group, a pentacene ring group, a perylene ring group, a pentaphene ring group, a picene ring group, a pyranthrene ring group, and an anthanthrene ring group.

Examples of the aromatic heterocyclic group include a furan ring group (furyl group), a thiophene ring group, a pyridine ring group (pyridyl group), a pyridazine ring group, a pyrimidine ring group, a pyrazine ring group, a pyrrole ring group (pyrrolyl group), a triazine ring group, an oxazole ring group (oxazolyl group), an oxadiazole ring group, a triazole ring group, an imidazole ring group (imidazolyl group), a pyrazole ring group, a thiazole ring group (thiazolyl group), an indole ring group, a benzimidazole ring group, a benzothiazole ring group, a benzoxazole ring group, a quinoxaline ring group, a quinazoline ring group, a phthalazine ring group, a benzofuran ring group, a dibenzofuran ring group, a benzothiophene ring group, a dibenzothiophene ring group, and a carbazole ring group.

These aromatic ring groups may each have the substituent (a) or (b). Specific examples of the substituents (a) and (b) include alkyl groups having 1 to 24 carbon atoms (such as a methyl group, an ethyl group, a propyl group, an isopropyl group, a t-butyl group, a pentyl group, a hexyl group, an octyl group, a decyl group, a dodecyl group, an octadecyl group, a cyclohexyl group, and a cyclopentyl group); alkoxy groups having 1 to 24 carbon atoms (such as a methoxy group, an ethoxy group, a propyloxy group, a pentyloxy group, a hexyloxy group, an octyloxy group, a decyloxy group, a dodecyloxy group, an octadecyloxy group, a cyclohexyloxy group, and a cyclopentyloxy group); an aromatic hydrocarbon group optionally having a substituent (c); an aromatic heterocyclic group optionally having a substituent (d); and halogen atoms (such as a chlorine atom, a bromine atom, an iodine atom, and a fluorine atom), aryloxy groups (such as a phenoxy group), alkoxycarbonyl groups (such as a methyloxycarbonyl group and an ethyloxycarbonyl group), sulfonamide groups (such as a methanesulfonamide group, an ethanesulfonamide group, a butanesulfonamide group, a hexanesulfonamide group, a cyclohexanesulfonamide group, and a benzenesulfonamide group), sulfamoyl groups (such as an aminosulfonyl group, a methylaminosulfonyl group, a dimethylaminosulfonyl group, a butylaminosulfonyl group, a hexylaminosulfonyl group, a cyclohexylaminosulfonyl group, a phenylaminosulfonyl group, and a 2-pyridylaminosulfonyl group), carbamoyl groups (such as an aminocarbonyl group, a methylaminocarbonyl group, a dimethylaminocarbonyl group, and a propylaminocarbonyl group), amide groups (such as an acetamide group, a propionamide group, and a benzamide group), sulfonyl groups (a methylsulfonyl group, an ethylsulfonyl group, and a phenylsulfonyl group), amino groups (such as an amino group, an ethylamino group, and a dimethylamino group), a cyano group, a carboxyl group, and a hydroxyl group.

In particular, the substituents (a) and (b) are each independently preferably an alkyl group having 1 to 18 (more preferably 4 to 12) carbon atoms, an alkoxy group having 1 to 18 (more preferably 4 to 12) carbon atoms, an aromatic hydrocarbon group optionally having the substituent (c), or an aromatic heterocyclic group optionally having the substituent (d). The number of carbon atoms of the alkyl group and the alkoxy group as the substituents (a) and (b) is preferably within the above-mentioned range, because the compound does not come into a wax-like state, and the compound has good compatibility with a binder resin when being added to a toner. A case where the substituents (a) and (b) are each an alkyl group or an alkoxy group is advantageous in that the π-π interaction between molecules can be further reduced. In addition, when an unsubstituted aromatic ring is introduced into the substituents (a) and (b), the compound is less likely to be fluidized and high light irradiation energy is required, because the it-t interaction between molecules is strong, and the alignment of molecules is less likely to be disordered. However, when the compound is added to a toner, the light irradiation energy can be reduced to a low level at the time of fixing, and combined use of pressurization and heating makes it possible to exhibit excellent softening rate and image fixability.

Further, when the aromatic ring is substituted with an alkyl group or an alkoxy group having thermal mobility, the propenimine compound can form a specific crystal structure in which, in a periodic structure dominated by the π-π interaction, a structure isotropically disturbed by thermal motion of the alkyl group or the alkoxy group coexists. Therefore, when the cis-trans isomerization reaction locally proceeds and the π-π interaction of the propenimine moiety is reduced, isotropic melting occurs in a chain manner in the entire system. Therefore, trans-cis isomerization of the propenimine compound is more likely to proceed, and fluidization is more likely to occur. Therefore, addition of the propenimine compound to a toner makes it possible to exhibit an appropriate softening rate and excellent image fixability even without the combined use of pressurization and heating and even with low light irradiation energy at the time of fixing.

The aromatic rings of the substituents (a) and (b) may have the substituent (c) and/or the substituent (d). Examples of the substituents (c) and (d) include alkyl groups having 1 to 8 (more preferably 1 to 3) carbon atoms (such as a methyl group, an ethyl group, a propyl group, an isopropyl group, a t-butyl group, a pentyl group, a hexyl group, a heptyl group, an octyl group, a cyclopentyl group, and a cyclohexyl group); and alkoxy groups having 1 to 8 (more preferably 1 to 3) carbon atoms (such as a methoxy group, an ethoxy group, a propyloxy group, a pentyloxy group, a hexyloxy group, an octyloxy group, a cyclopentyloxy group, and a cyclohexyloxy group). When the number of carbon atoms of the alkyl group and the alkoxy group as the substituents (c) and (d) is 1 or more and 8 or less, the propenimine compound does not have too high a molecular weight, and therefore, in a toner containing the compound, the compound has good compatibility with and solubility in the binder resin. The reason why an alkyl group or an alkoxy group is introduced as the substituents (c) and (d) is as follows. Specifically, when a bulky substituent such as a halogen atom, a nitro group, a cyano group, or a dialkylamino group is introduced as the substituent (c) or (d), use of the propenimine compound having the substituent in a toner is disadvantageous in terms of compatibility with the binder resin, and the electron-withdrawing substituent such as a halogen atom, a nitro group, or a cyano group may adversely affect the photoisomerization reaction. Therefore, it is preferred to introduce an alkyl group or alkoxy group having a small number of carbon atoms, because the group is a less bulky substituent that is less likely to cause such a phenomenon, is electron-donating, and facilitates the production of the propenimine compound. Thus, in a toner containing the propenimine compound having the substituents, the compound has good compatibility with the binder resin, and moreover, the compound can be easily fluidized by light irradiation and can be reversibly non-fluidized since the electron-donating substituents are introduced into the compound.

The numbers of the substituents (a) and (b) other than a hydrogen atom that are introduced into the aromatic rings are each preferably 1 or more and 5 or less. However, from the viewpoint that the melting point decreases and the heat-resistant storage stability of the toner is improved as the numbers of substituents increases, the numbers of the substituents (a) and (b) other than a hydrogen atom are each more preferably 1 or more and 2 or less.

In the general formula (1), Y, $Z_1$, and $Z_2$ are each independently a hydrogen atom or a lower alkyl group. This is because introduction of a large substituent at the positions of Y, $Z_1$, and $Z_2$ in the general formula (1) is difficult in terms of synthesis, and even if synthesis is possible, steric hindrance occurs during the photoisomerization, and therefore it is preferred to avoid such introduction as much as possible. Introduction of a small substituent such as a hydrogen atom or a lower alkyl group at the positions of Y, $Z_1$, and $Z_2$ is advantageous in that the above-mentioned problems hardly occur. Here, the lower alkyl group is a linear or branched alkyl group (such as a methyl group, an ethyl group, a propyl group, an isopropyl group, a t-butyl group, a pentyl group, and a hexyl group) having 1 to 6 (preferably 1 to 4) carbon atoms. When the introduced substituents are small, the compound can be easily synthesized with small steric hindrance and easily secures free volume required for a cis-trans isomerization reaction, and steric hindrance during the photoisomerization hardly occurs. From such a viewpoint, an alkyl group having 1 to 2 carbon atoms is more preferred.

At least one of Y, $Z_1$, and $Z_2$, preferably one or more and two or less of Y, $Z_1$, and $Z_2$ are a linear or branched alkyl group having 1 to 6 carbon atoms. The alkyl group is more preferably an alkyl group having 1 to 4 carbon atoms, and still more preferably an alkyl group having 1 to 2 carbon atoms. The reason why such cases are preferred is that such cases induce generation of lattice defects, production of free volume, and reduction of a π-π interaction between molecules, which act favorably for cis-trans isomerization.

Examples of the propenimine compound of the present invention include Compound Nos. 1 to 57 in which aromatic rings A (an aromatic hydrocarbon group or an aromatic heterocyclic group), $R_1$ to $R_{10}$ that are the substituents (a) and (b) of the aromatic rings, X (a hetero group), Y, $Z_1$, and $Z_2$ are appropriately selected in the general formula (1) as shown in Tables 1-1 to 1-5 shown below. Table 1-5 also shows Comparative Compounds 1 and 2 that are an azobenzene compound used in the section of Examples of JP 2011-256155 A (corresponding to US 2013/0066068 A), and a stilbene compound, respectively.

TABLE 1-1

| Compound No. | $R_1$ | $R_2$ | $R_3$ | $R_4$ | $R_5$ | $R_6$ | $R_7$ | $R_8$ | $R_9$ | $R_{10}$ | Y | $Z_1$ | $Z_2$ |
|---|---|---|---|---|---|---|---|---|---|---|---|---|---|
| 1 | H | H | $C_4H_9$ | H | H | H | H | $C_5H_{11}$ | H | H | H | H | H |
| 2 | H | H | $C_6H_{13}$ | H | H | H | H | $OC_6H_{13}$ | H | H | H | H | H |
| 3 | H | H | $C_{10}H_{21}$ | H | H | H | H | $C_4H_9$ | H | H | H | H | $CH_3$ |
| 4 | H | H | $OC_4H_9$ | H | H | H | H | $C_8H_{17}$ | H | H | H | H | H |
| 5 | H | H | $OC_6H_{13}$ | H | H | H | H | $OC_6H_{13}$ | H | H | H | H | H |
| 6 | H | H | $OC_6H_{13}$ | H | H | H | $C_2H_5$ | H | $C_2H_5$ | H | H | H | H |
| 7 | H | H | $OC_{11}H_{23}$ | H | H | H | H | $C_{10}H_{21}$ | H | H | H | $C_2H_5$ | H |
| 8 | $C_4H_9$ | H | $C_5H_{11}$ | H | H | H | H | $OC_4H_9$ | H | H | H | H | H |
| 9 | H | $C_7H_{15}$ | $C_7H_{15}$ | H | H | H | $C_7H_{15}$ | $C_7H_{15}$ | H | H | H | H | H |
| 10 | H | $C_8H_{17}$ | H | $C_8H_{17}$ | H | H | H | $OC_5H_{11}$ | H | H | $CH_3$ | H | H |
| 11 | H | H | $OC_4H_9$ | H | H | H | H | H | $C_{13}H_{27}$ | H | H | H | H |
| 12 | H | $C_3H_7$ | H | $C_3H_7$ | H | H | H | $OC_{15}H_{31}$ | H | H | H | H | H |
| 13 | H | H | $C_{18}H_{37}$ | H | H | H | H | H | H | H | H | H | H |

TABLE 1-2

| Compound No. | A | $R_1$ | $R_2$ | $R_3$ | $R_4$ | $R_5$ | $R_6$ | $R_7$ | $R_8$ | $R_9$ | Y | $Z_1$ | $Z_2$ |
|---|---|---|---|---|---|---|---|---|---|---|---|---|---|
| 14 | $A_1$ | H | H | $C_6H_{13}$ | H | H | H | $OC_6H_{13}$ | H | H | H | H | H |
| 15 | | H | H | $OC_8H_{17}$ | H | H | H | $OC_4H_9$ | H | H | H | H | H |
| 16 | | H | $C_4H_9$ | H | $C_4H_9$ | H | $C_4H_9$ | H | $C_4H_9$ | H | H | H | H |
| 17 | | H | H | $OC_{12}H_{25}$ | H | H | H | Ph | H | $CH_3$ | H | H | H |
| 18 | $A_2$ | $OC_5H_{11}$ | H | H | H | H | H | $OC_9H_{19}$ | H | H | H | $C_2H_5$ | H |
| 19 | | H | H | $OC_6H_{13}$ | H | H | H | $OC_6H_{13}$ | H | H | H | H | H |
| 20 | | H | H | $C_4H_9$ | H | H | H | H | H | $C_4H_9$ | H | H | H |
| 21 | | $C_7H_{15}$ | H | H | $C_7H_{15}$ | H | H | H | H | H | H | H | H |
| 22 | | H | $C_4H_9$ | H | H | H | H | $OC_{11}H_{23}$ | H | H | $CH_3$ | H | H |
| 23 | $A_3$ | H | H | $OC_9H_{19}$ | H | H | H | $OC_4H_9$ | $OC_4H_9$ | H | H | H | H |
| 24 | | H | $OC_4H_9$ | H | $OC_4H_9$ | H | H | H | H | $C_8H_{17}$ | H | H | H |
| 25 | | H | H | $C_8H_{17}$ | H | H | H | H | H | H | H | H | $CH_3$ |
| 26 | | H | H | $C_{14}H_{29}$ | H | H | H | H | H | H | $CH_3$ | H | H |

TABLE 1-3

| Compound No. | A | X | $R_1$ | $R_2$ | $R_3$ | $R_4$ | $R_5$ | $R_6$ | $R_7$ | $R_8$ | Y | $Z_1$ | $Z_2$ |
|---|---|---|---|---|---|---|---|---|---|---|---|---|---|
| 27 | $A_1$ | S | $CH_3$ | H | H | H | H | $OC_6H_{13}$ | H | H | H | H | H |
| 28 | | | H | $CH_3$ | $CH_3$ | H | H | $C_8H_{17}$ | H | H | H | H | H |

TABLE 1-3-continued

| Compound No. | A | X | $R_1$ | $R_2$ | $R_3$ | $R_4$ | $R_5$ | $R_6$ | $R_7$ | $R_8$ | Y | $Z_1$ | $Z_2$ |
|---|---|---|---|---|---|---|---|---|---|---|---|---|---|
| 29 | $A_2$ |  | H | $C_2H_5$ | H | H | H | $OC_{12}H_{25}$ | H | H | H | H | $CH_3$ |
| 30 |  |  | $CH_3$ | H | $CH_3$ | H | $C_4H_9$ | H | $C_4H_9$ | H | H | H | H |
| 31 | $A_1$ | O | H | H | H | H | H | $OC_6H_{13}$ | H | H | H | H | H |
| 32 |  |  | H | $CH_3$ | H | H | $OC_4H_9$ | H | H | H | $CH_3$ | H | H |
| 33 | $A_2$ |  | H | H | H | H | H | $OC_9H_{19}$ | H | H | H | $C_2H_5$ | H |
| 34 |  |  | H | H | H | $CH_3$ | H | $OC_5H_{11}$ | H | $CH_3$ | H | H | H |
| 35 | $A_1$ | NH | $CH_3$ | H | H | H | H | $OC_9H_{19}$ | H | H | H | H | H |
| 36 | $A_2$ |  | H | $C_2H_5$ | H | H | $C_{10}H_{21}$ | H | H | H | H | H | H |
| 37 | $A_1$ | $NCH_3$ | H | H | H | H | H | $OC_6H_{13}$ | H | H | H | H | H |
| 38 |  |  | H | H | $CH_3$ | H | $C_8H_{17}$ | H | H | H | $CH_3$ | H | H |
| 39 | $A_2$ |  | $CH_3$ | H | H | H | H | $C_{11}H_{23}$ | H | H | H | H | H |
| 40 |  |  | $CH_3$ | H | H | H | H | $OC_{16}H_{33}$ | H | H | H | H | H |

TABLE 1-4

| Compound No. | A | X | $R_1$ | $R_2$ | $R_3$ | $R_4$ | $R_5$ | $R_6$ | $R_7$ | $R_8$ | Y | $Z_1$ | $Z_2$ |
|---|---|---|---|---|---|---|---|---|---|---|---|---|---|
| 41 | $A_1$ | S | $CH_3$ | H | H | H | H | $OC_8H_{17}$ | H | H | H | $CH_3$ | H |
| 42 |  |  | H | $C_2H_5$ | H | H | H | H | $C_{10}H_{21}$ | H | H | H | H |
| 43 | $A_2$ |  | H | H | $CH_3$ | H | H | $OC_{12}H_{25}$ | H | H | H | H | H |
| 44 | $A_1$ | O | H | H | H | H | H | $OC_6H_{13}$ | H | H | H | H | H |
| 45 |  |  | H | H | $CH_3$ | H | H | H | $OC_{10}H_{21}$ | H | H | H | H |
| 46 | $A_2$ |  | H | $C_2H_5$ | H | H | H | $C_9H_{19}$ | H | H | $CH_3$ | H | H |
| 47 |  |  | H | H | H | $C_4H_9$ | H | $C_4H_9$ | H | H | H | H | H |
| 48 | $A_1$ | NH | H | H | $C_2H_5$ | $OC_4H_9$ | H | H | $OC_4H_9$ | H | H | H | H |
| 49 | $A_2$ |  | $CH_3$ | H | H | H | H | $OC_5H_{11}$ | H | H | H | H | $C_2H_5$ |
| 50 | $A_1$ | $NCH_3$ | H | H | H | $C_4H_9$ | $OC_8H_{17}$ | $C_4H_9$ | H | H | H | H | H |
| 51 |  | $NC_2H_5$ | H | H | $CH_3$ | H | H | $OC_6H_{13}$ | H | H | H | H | H |
| 52 | $A_2$ | $NCH_3$ | H | $C_2H_5$ | H | H | H | $C_7H_{15}$ | H | H | $CH_3$ | H | H |
| 53 |  |  | H | $CH_3$ | H | H | H | $OC_{17}H_{35}$ | H | H | H | H | H |

TABLE 1-5

| Compound No. | |
|---|---|
| 54 | 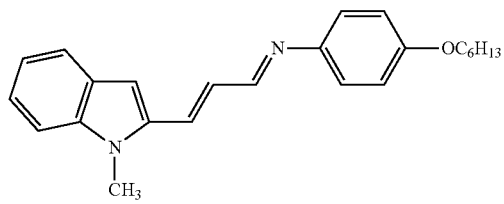 |
| 55 | 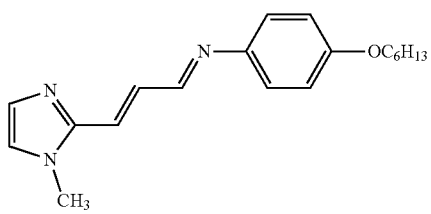 |
| 56 | 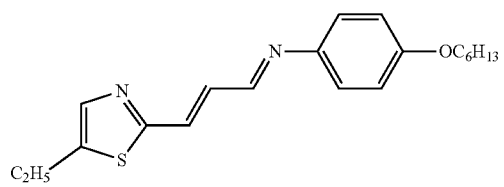 |
| 57 | 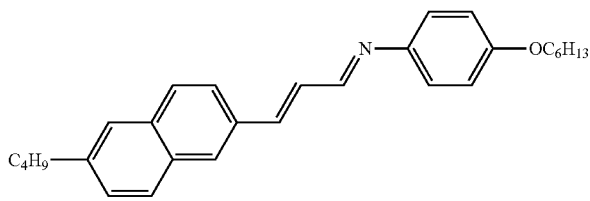 |
| Comparative Compound | |
| 1 | 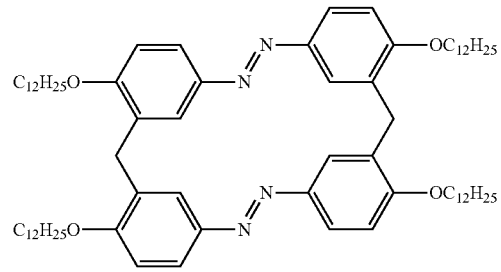 |
| 2 | 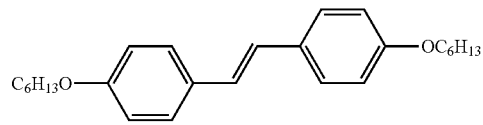 |

As described above, both the alkyl group and the alkoxy group as the substituents ($R_1$ to $R_{10}$) of the aromatic rings may be linear or branched.

The molecular weight of the compound represented by the general formula (1) is not particularly limited, but is preferably 100 or more and 1000 or less, more preferably 200 or more and 850 or less, more preferably 300 or more and 750 or less, and still more preferably 500 or more and 600 or less. The compound represented by the general formula (1) does not contain a polymer. In a preferred embodiment, the compound represented by the general formula (1) does not contain a repeating unit. In a preferred embodiment, the propenimine compound represented by the general formula (1) is not a compound that is obtained by polymerizing monomers containing a polymerizable group.

The irradiation light at the time of fluidizing the propenimine compound of the present invention by light irradiation preferably has a wavelength in the range of 280 nm or more and 420 nm or less, more preferably in the range of 300 nm or more and 400 nm or less, and still more preferably in the range of 330 nm or more and 390 nm or less. When the wavelength is within the above-mentioned range, the compound well absorbs light mainly in the ultraviolet region and has improved light melting property, and a toner containing the compound has improved fixability. Examples of a light source suitable for applying the ultraviolet light include a light emitting diode (LED) and a laser light source. At the time of fluidizing the compound, heat or pressure may be applied to the compound in addition to light irradiation to promote fluidization. Application of heat or pressure makes it possible to fluidize the compound with a smaller light irradiation amount. Therefore, addition of the propenimine compound to a toner provides a toner that can be fixed by light irradiation at the above-mentioned wavelength and has high color reproducibility even when a colorant is mixed with the compound. The above-mentioned wavelength range is a region of ultraviolet light, but also includes a region of visible light near ultraviolet light. Even with irradiation light in a region of visible light near ultraviolet light, the propenimine compound can be fluidized under the following irradiation conditions.

The light irradiation amount at the time of fluidizing the propenimine compound is preferably in the range of 0.1 J/cm² or more and 200 J/cm² or less, more preferably in the range of 0.5 J/cm² or more and 100 J/cm² or less, and still more preferably in the range of 1.0 J/cm² or more and 50 J/cm² or less. When the light irradiation amount is 0.1 J/cm² or more, a reaction of E→Z occurs beyond the energy barrier, and the propenimine compound has improved light melting property, so that the compound can be fluidized. Meanwhile, when the light irradiation amount is 200 J/cm² or less, the energy is not too large, and the propenimine compound can be satisfactorily fluidized without being broken.

Meanwhile, at the time of reversibly non-fluidizing the propenimine compound, as shown in the section of Examples, it is not necessary to apply external force (external energy) such as light, heat, or pressure, but light irradiation as described below may be performed. From the viewpoint of weight and size reduction and simplification of an image forming apparatus, energy saving, and prevention of global warming by reduction of exhaust heat and CO₂, it is preferred to reversibly non-fluidize the propenimine compound without applying external energy or external force such as light irradiation, heating, and pressurization.

At the time of irradiating the propenimine compound with light to reversibly non-fluidize the propenimine compound, it is preferred that the irradiation light have a wavelength longer than that of the irradiation light at the time of fluidizing the propenimine compound. Specifically, the wavelength of the irradiation light is, for example, in the range of 400 nm or more and 800 nm or less, preferably in the range of more than 420 nm and 800 nm or less, more preferably in the range of 430 nm or more and 730 nm or less, and still more preferably in the range of 450 nm or more and 650 nm or less. When the wavelength is within the above-mentioned range, the compound well absorbs light mainly in the visible light region and has improved photocurability, and a toner containing the compound has improved fixability. Further, when the compound is irradiated with the irradiation light having the above-mentioned wavelength, it is possible to non-fluidize the compound without applying heat or pressure. Therefore, addition of the propenimine compound to a toner makes it possible to solidify a toner image on a recording sheet more reliably, further improve the fixability of the toner image to the recording sheet, and provide a toner having high color reproducibility.

The light irradiation amount at the time of irradiating the propenimine compound with light to non-fluidize the propenimine compound is preferably in the range of 0.1 J/cm² or more and 200 J/cm² or less, more preferably in the range of 0.5 J/cm² or more and 100 J/cm² or less, and still more preferably in the range of 1.0 J/cm² or more and 50 J/cm² or less. When the light irradiation amount is 0.1 J/cm² or more, a reaction of Z→E occurs beyond the energy barrier, so that the propenimine compound can be non-fluidized. Meanwhile, when the light irradiation amount is 200 J/cm² or less, the energy is not too large, the propenimine compound can be satisfactorily non-fluidized without being broken, and the toner can be reliably solidified.

In addition, as for a means for reversibly non-fluidizing the propenimine compound, as described above, it is most preferred to leave the propenimine compound at room temperature (without heating; 25±15° C.), that is, place the propenimine compound in a natural environment without applying external energy or external force such as light irradiation, heating, and pressurization. In this case, it is preferred to place the propenimine compound in a dark place, but the propenimine compound may receive natural light or visible light from a fluorescent lamp or the like. Note that, in the case of non-fluidizing the propenimine compound using some means, it is preferred to use a means by light irradiation. With use of such a means, the propenimine compound can be reversibly non-fluidized in a short time, and the weight and size of an image forming apparatus, particularly a fixing device can be reduced.

A method for synthesizing the propenimine compound of the present invention is not particularly limited, and conventionally known synthesis methods can be applied. For example, Compound No. 5 of the general formula (1) shown in Table 1-1 can be synthesized by the following method.

[Chemical Formula 4]

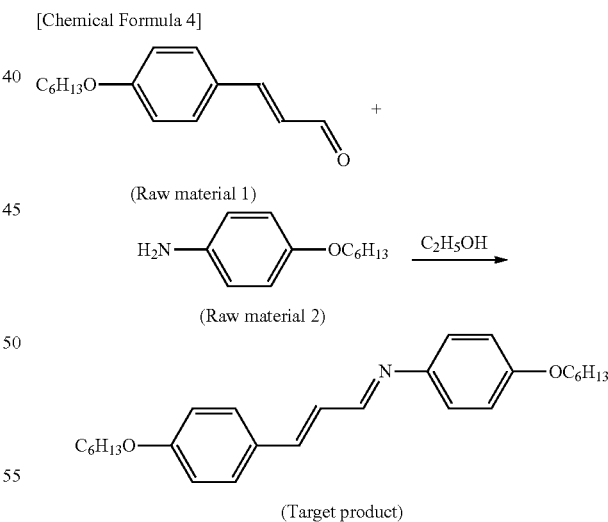

In ethanol (hereinafter also referred to as EtOH), 3-(4-(hexyloxy)phenyl)acetylaldehyde (raw material 1) and 4-hexyloxyaniline (raw material 2) are stirred and heated to reflux. The disappearance of 4-hexyloxyaniline is confirmed, then the internal temperature is lowered to room temperature, and the reaction liquid is added to water to stop the reaction. The target product is extracted with ethyl acetate, washed with water, and the ethyl acetate solution is dried and then concentrated to give crude crystals of Compound No. 5. The crude crystals are recrystallized from EtOH to give Compound No. 5 as the target product.

Propenimine compounds other than Compound No. 5 can also be synthesized in the same manner as in the synthesis of Compound No. 5 described above. Specifically, Compound Nos. 1 to 4 and 6 to 57 as target products can be synthesized in the same manner as in the synthesis of Compound No. 5 except that 3-(4-(hexyloxy)phenyl)acetylaldehyde (raw material 1) and 4-hexyloxyaniline (raw material 2) are respectively changed to acetylaldehyde (raw material 1) and aniline (raw material 2) shown in Tables 2-1 to 2-3 in the section of Examples.

The propenimine compound of the present invention may be used alone or in combination of two or more.

[Configuration of Toner]

The toner of the present invention contains the propenimine compound that is colorless and is fluidized by light irradiation and reversibly non-fluidized. Addition of the propenimine compound to the toner does not affect the desired color reproduction even when the propenimine compound is mixed with a colorant, can remarkably improve the softening rate of the toner by light irradiation, and can maintain the softened state necessary for fixing, so that image fixability is improved. The term "toner(s)" refers to an aggregate of toner base particles or toner particles. The toner particles are preferably obtained by adding an external additive to the toner base particles, but the toner base particles can be used as toner particles as they are. In the present invention, when it is not necessary to particularly distinguish among the toner base particles, the toner particles, and the toner, they are also simply referred to as "toner(s)".

<Binder Resin>

The toner of the present invention preferably further contains a binder resin in addition to the propenimine compound. It is generally known that use of an emulsion aggregation method described later as a method for producing a toner provides toner particles having a substantially uniform particle size and a substantially uniform shape. A toner can be produced without using the binder resin by using the propenimine compound alone or adding a colorant or a release agent as another additive to the propenimine compound (see Example 83 in Table 4-2). However, combined use of the propenimine compound and the binder resin makes it possible to produce toner particles having a substantially uniform particle size and a substantially uniform shape using salting-out in the emulsion aggregation method. Therefore, the toner containing the propenimine compound and the binder resin can be applied to an electrophotographic toner more easily.

As for the binder resin, a resin generally used as a binder resin that constitutes a toner can be used without limitation. Specific examples of the resin include a styrene resin, an acrylic resin, a styrene-acrylic resin, a polyester resin, a silicone resin, an olefin resin, an amide resin, and an epoxy resin. These binder resins may be used alone or in combination of two or more.

Among them, the binder resin preferably includes at least one selected from the group consisting of a styrene resin, an acrylic resin, a styrene-acrylic resin, and a polyester resin, and more preferably includes at least one selected from the group consisting of a styrene-acrylic resin and a polyester resin, from the viewpoint that the resin has a low viscosity when melted and has a high sharp melting property.

Hereinafter, a styrene-acrylic resin (also referred to as a styrene acrylic resin) and a polyester resin that are preferred binder resins will be described.

(Styrene-Acrylic Resin)

The styrene acrylic resin referred to herein is formed by polymerizing at least a styrene monomer and a (meth)acrylic acid ester monomer. Here, examples of the styrene monomer include, in addition to styrene represented by the structural formula $CH_2=CH-C_6H_5$, a styrene monomer having a structure including, in a styrene structure, a known side chain or functional group.

The (meth)acrylic acid ester monomer has, in a side chain, a functional group having an ester bond. Specific examples of the (meth)acrylic acid ester monomer include, in addition to an acrylic acid ester monomer represented by $CH_2=CHCOOR$ (wherein R is an alkyl group), vinyl ester compounds such as a methacrylic acid ester monomer represented by $CH_2=C(CH_3)COOR$ (wherein R is an alkyl group).

Hereinafter, specific examples of the styrene monomer and the (meth)acrylic acid ester monomer capable of forming the styrene acrylic resin will be given, but the styrene monomer and the (meth)acrylic acid ester monomer are not limited to those given below.

Examples of the styrene monomer include styrene, o-methylstyrene, m-methylstyrene, p-methylstyrene, α-methylstyrene, p-phenylstyrene, p-ethylstyrene, 2,4-dimethylstyrene, p-t-butylstyrene, p-n-hexylstyrene, p-n-octylstyrene, p-n-nonylstyrene, p-n-decylstyrene, and p-n-dodecylstyrene.

Typical examples of the (meth)acrylic acid ester monomer include the following acrylic acid ester monomers and methacrylic acid ester monomers, and examples of the acrylic acid ester monomer include methyl acrylate, ethyl acrylate, n-propyl acrylate, isopropyl acrylate, n-butyl acrylate, isobutyl acrylate, t-butyl acrylate, n-octyl acrylate, 2-ethylhexyl acrylate, stearyl acrylate, lauryl acrylate, and phenyl acrylate. Examples of the methacrylic acid ester monomer include methyl methacrylate, ethyl methacrylate, n-propyl methacrylate, isopropyl methacrylate, n-butyl methacrylate, isobutyl methacrylate, t-butyl methacrylate, n-octyl methacrylate, 2-ethylhexyl methacrylate, stearyl methacrylate, lauryl methacrylate, phenyl methacrylate, diethylaminoethyl methacrylate, and dimethylaminoethyl methacrylate.

All of the styrene monomer, acrylic acid ester monomer, and methacrylic acid ester monomer may be used alone or in combination of two or more.

In addition, examples of the styrene acrylic copolymer include, in addition to the above-mentioned copolymer formed only of the styrene monomer and the (meth)acrylic acid ester monomer, copolymers formed by using, in addition to the styrene monomer and the (meth)acrylic acid ester monomer, a general vinyl monomer in combination. Hereinafter, examples of the vinyl monomer that can be used in combination in forming the styrene acrylic copolymer referred to herein will be given, but the vinyl monomer that can be used in combination is not limited to those given below.

(1) Olefins
   Ethylene, propylene, isobutylene, and the like
(2) Vinyl Esters
   Vinyl propionate, vinyl acetate, vinyl benzoate, and the like
(3) Vinyl Ethers
   Vinyl methyl ether, vinyl ethyl ether, and the like
(4) Vinyl Ketones
   Vinyl methyl ketone, vinyl ethyl ketone, vinyl hexyl ketone, and the like (5) N-Vinyl Compounds
N-vinylcarbazole, N-vinylindole, N-vinylpyrrolidone, and the like
(6) Others
Vinyl compounds such as vinylnaphthalene and vinylpyridine, acrylic acid or methacrylic acid derivatives such as acrylonitrile, methacrylonitrile, and acrylamide, and the like In addition, it is also possible to produce a resin having a crosslinked structure using a polyfunctional vinyl monomer. Further, it is also possible to use a vinyl monomer having an ionic dissociation group in a side chain. Specific examples of the ionic dissociation group include a carboxyl group, a sulfonic acid group, and a phosphoric acid group. Specific examples of the vinyl monomer having the ionic dissociation group will be given below.

Specific examples of the vinyl monomer having a carboxyl group include acrylic acid, methacrylic acid, maleic acid, itaconic acid, cinnamic acid, fumaric acid, maleic acid monoalkyl ester, and itaconic acid monoalkyl ester.

A method for forming the styrene acrylic resin is not particularly limited, and examples thereof include a method of polymerizing the monomers using a known oil-soluble or water-soluble polymerization initiator. If necessary, for example, a known chain transfer agent such as n-octyl mercaptan may be used.

In the formation of the styrene acrylic resin used in the present invention, the contents of the styrene monomer and the acrylic acid ester monomer are not particularly limited, and can be appropriately adjusted from the viewpoint of controlling the softening temperature and the glass transition temperature of the binder resin. Specifically, the content of the styrene monomer is preferably 40 mass % or more and 95 mass % or less, and more preferably 50 mass % or more and 90 mass % or less based on the entire monomers. In addition, the content of the acrylic acid ester monomer is preferably 5 mass % or more and 60 mass % or less, and more preferably 10 mass % or more and 50 mass % or less based on the entire monomers.

A method for forming the styrene acrylic resin is not particularly limited, and examples thereof include a method of polymerizing the monomers using a known oil-soluble or water-soluble polymerization initiator. Specific examples of the oil-soluble polymerization initiator include azo or diazo polymerization initiators and peroxide polymerization initiators described below.

Examples of the azo or diazo polymerization initiator include 2,2'-azobis-(2,4-dimethylvaleronitrile), 2,2'-azobisisobutyronitrile, 1,1'-azobis(cyclohexane-1-carbonitrile), 2,2'-azobis-4-methoxy-2,4-dimethylvaleronitrile, and azobisisobutyronitrile.

Examples of the peroxide polymerization initiator include benzoyl peroxide, methyl ethyl ketone peroxide, diisopropyl peroxycarbonate, cumene hydroperoxide, t-butyl hydroperoxide, di-t-butyl peroxide, dicumyl peroxide, 2,4-dichlorobenzoyl peroxide, lauroyl peroxide, 2,2-bis-(4,4-t-butylperoxycyclohexyl)propane, and tris-(t-butylperoxy)triazine.

When forming styrene acrylic resin particles by an emulsion polymerization method, a water-soluble radical polymerization initiator can be used. Examples of the water-soluble radical polymerization initiator include persulfates such as potassium persulfate and ammonium persulfate, azobisaminodipropane acetate, azobiscyanovaleric acid and salts thereof, and hydrogen peroxide.

The polymerization temperature varies depending on the type of the monomers and polymerization initiator used, but is preferably in the range of 50° C. or more and 100° C. or less, and more preferably in the range of 55° C. or more and 90° C. or less. The polymerization time varies depending on the type of the monomers and polymerization initiator used, but is preferably in the range of 2 hours or more and 12 hours or less, for example.

The styrene acrylic resin particles formed by the emulsion polymerization method may have a structure including two or more layers containing resins having different compositions. As for a production method in this case, it is possible to adopt a multi-stage polymerization method in which a polymerization initiator and polymerizable monomers are added to a dispersion liquid of resin particles prepared by an emulsion polymerization treatment (first stage polymerization) according to a routine method, and the resulting system is subjected to a polymerization treatment (second stage polymerization).

(Polyester Resin)

The polyester resin is a known polyester resin obtained by a polycondensation reaction of a divalent or higher carboxylic acid (polyvalent carboxylic acid component) and a dihydric or higher alcohol (polyhydric alcohol component). The polyester resin may be amorphous or crystalline.

Since each of the polyvalent carboxylic acid component and the polyhydric alcohol component preferably has a valence of 2 or more and 3 or less, and particularly preferably has a valence of 2, a dicarboxylic acid component and a diol component each having a valence of 2 will be described as a particularly preferred embodiment.

Examples of the dicarboxylic acid component include saturated aliphatic dicarboxylic acids such as oxalic acid, malonic acid, succinic acid, glutaric acid, adipic acid, pimelic acid, suberic acid, azelaic acid, sebacic acid, 1,9-nonanedicarboxylic acid, 1,10-decanedicarboxylic acid (dodecanedioic acid), 1,11-undecanedicarboxylic acid, 1,12-dodecanedicarboxylic acid, 1,13-tridecanedicarboxylic acid, 1,14-tetradecanedicarboxylic acid, 1,16-hexadecanedicarboxylic acid, and 1,18-octadecanedicarboxylic acid; unsaturated aliphatic dicarboxylic acids such as methylene succinic acid, fumaric acid, maleic acid, 3-hexenedioic acid, 3-octenedioic acid, and dodecenylsuccinic acid; and unsaturated aromatic dicarboxylic acids such as phthalic acid, terephthalic acid, isophthalic acid, t-butylisophthalic acid, tetrachlorophthalic acid, chlorophthalic acid, nitrophthalic acid, p-phenylenediacetic acid, 2,6-naphthalenedicarboxylic acid, 4,4'-biphenyldicarboxylic acid, and anthracenedicarboxylic acid. Lower alkyl esters and acid anhydrides of the above-mentioned compounds can also be used. The dicarboxylic acid component may be used alone or in combination of two or more.

It is also possible to use, in addition to the dicarboxylic acid component, trivalent or higher polyvalent carboxylic acids such as trimellitic acid and pyromellitic acid, anhydrides of the polyvalent carboxylic acids, and esters of the polyvalent carboxylic acids having an alkyl group having 1 to 3 carbon atoms.

Examples of the diol component include saturated aliphatic diols such as ethylene glycol, 1,2-propanediol, 1,3-propanediol, 1,4-butanediol, 1,5-pentanediol, 1,6-hexanediol, 1,7-heptanediol, 1,8-octanediol, 1,9-nonanediol, 1,10-decanediol, 1,11-undecanediol, 1,12-dodecanediol, 1,13-tridecanediol, 1,14-tetradecanediol, 1,18-octadecanediol, 1,20-eicosanediol, and neopentyl glycol; unsaturated aliphatic diols such as 2-butene-1,4-diol, 3-butene-1,4-diol, 2-butyne-1,4-diol, 3-butyne-1,4-diol, and 9-octadecene-7,12-diol; and aromatic diols including bisphenols such as bisphenol A and bisphenol F, and alkylene oxide adducts of bisphenols such as ethylene oxide adducts and propylene oxide adducts of the bisphenols. Derivatives of the above-mentioned compounds can also be used. The diol component may be used alone or in combination of two or more.

A method for producing the polyester resin is not particularly limited, and the polyester resin can be produced by polycondensation (esterification) of the polyvalent carboxylic acid component and the polyhydric alcohol component using a known esterification catalyst.

Examples of the catalyst usable in the production of the polyester resin include compounds of alkali metals such as sodium and lithium; compounds containing Group 2 elements such as magnesium and calcium; compounds of metals such as aluminum, zinc, manganese, antimony, titanium, tin, zirconium, and germanium; phosphorus acid compounds; phosphoric acid compounds; and amine compounds. Specific examples of the tin compound include dibutyltin oxide, tin octylate, tin dioctylate, and salts of these compounds. Examples of the titanium compound include titanium alkoxides such as tetra-n-butyl titanate (Ti(O-n-Bu)$_4$), tetraisopropyl titanate, tetramethyl titanate, and tetrastearyl titanate; titanium acylates such as polyhydroxytitanium stearate; and titanium chelates such as titanium tetraacetylacetonate, titanium lactate, and titanium triethanolaminate. Examples of the germanium compound include germanium dioxide. Further, examples of the aluminum compound include polyaluminum hydroxide, aluminum alkoxide, and tributyl aluminate. These catalysts may be used alone or in combination of two or more.

The polymerization temperature is not particularly limited, but is preferably in the range of 70° C. or more and 250° C. or less. The polymerization time is also not particularly limited, but is preferably in the range of 0.5 hour or more and 10 hours or less. During the polymerization, the pressure in the reaction system may be reduced as necessary.

When the toner of the present invention contains the propenimine compound and the binder resin, the content ratio between the propenimine compound and the binder resin depends on the compound type and the resin type, but the content ratio of the propenimine compound:the binder resin is preferably in the range of 5:95 to 80:20 (mass ratio) from the viewpoint of fixability and color reproducibility. When the content ratio is within the above-mentioned range, the optical phase transition of the propenimine compound is likely to occur, and a sufficient softening rate of the toner is achieved by light irradiation. From such a viewpoint, the range of the content ratio of the propenimine compound:the binder resin is more preferably 10:90 to 70:30 (mass ratio), and still more preferably 30:70 to 60:40 (mass ratio).

The toner containing the propenimine compound and the binder resin may have a single layer structure or a core-shell structure. The type of the binder resin used in the core particles and the shell portion of the core-shell structure is not particularly limited.

The glass transition temperature Tg of the binder resin is preferably in the range of 35° C. or more and 70° C. or less, and more preferably in the range of 40° C. or more and 60° C. or less from the viewpoint of heat-resistant storage stability and the like.

Here, the glass transition temperature Tg can be adjusted, for example, by appropriately selecting the type of monomers used in synthesis of the binder resin (binder) based on the glass transition temperature of the amorphous resin alone, or adjusting the copolymerization ratio (mass ratio) of the monomers or the molecular weight. For example, taking a styrene-(meth)acrylate copolymer as an example, the Tg can be lowered by increasing the copolymerization ratio (mass ratio) of n-butyl acrylate having a lower glass transition temperature based on the entire monomers, and the Tg can be increased by increasing the copolymerization ratio (mass ratio) of styrene having a higher glass transition temperature. In addition, taking an amorphous polyester resin as an example, the glass transition temperature can be controlled by adjusting the types of the dicarboxylic acid component and the diol component as well as the mixing ratio (mass ratio) between the components. Further, the glass transition temperature can be increased, for example, by copolymerizing a trifunctional or higher polyfunctional monomer such as trimellitic acid at an arbitrary polymerization ratio (mass ratio) to cause crosslinking in a molecule or between molecules.

<Colorant>

The toner of the present invention preferably further contains a colorant. The propenimine compound can induce reversible fluidization and non-fluidization phenomena due to photoisomerization while being colorless. Therefore, introduction of the propenimine compound together with a desired colorant into a toner provides a toner that can be fixed by light irradiation and has high color reproducibility of the added colorant. As for the colorant, generally known dyes and pigments can be used.

Examples of the colorant for obtaining a black toner include carbon black, magnetic materials, and iron-titanium composite oxide black. Examples of the carbon black include channel black, furnace black, acetylene black, thermal black, and lamp black. Examples of the magnetic material include ferrite and magnetite.

Examples of the colorant for obtaining a yellow toner include dyes such as C.I. Solvent Yellow 19, 44, 77, 79, 81, 82, 93, 98, 103, 104, 112, and 162; and pigments such as C.I. Pigment Yellow 14, 17, 74, 93, 94, 138, 155, 180, and 185.

Examples of the colorant for obtaining a magenta toner include dyes such as C.I. Solvent Red 1, 49, 52, 58, 63, 111, and 122; and pigments such as C.I. Pigment Red 5, 48:1, 53:1, 57:1, 122, 139, 144, 149, 166, 177, 178, and 222.

Examples of the colorant for obtaining a cyan toner include dyes such as C.I. Solvent Blue 25, 36, 60, 70, 93, and 95; and pigments such as C.I. Pigment Blue 1, 7, 15, 15:3, 60, 62, 66, and 76.

The colorant for obtaining the toner of each color may be used alone or in combination of two or more for each color.

The content ratio of the colorant in the toner is preferably in the range of 0.5 mass % or more and 20 mass % or less, and more preferably in the range of 2 mass % or more and 10 mass % or less.

<Release Agent>

The toner according to the present invention preferably further contains a release agent. Introduction of the release agent together with the propenimine compound into a toner provides a toner having more excellent fixability.

The release agent used is not particularly limited, and various known waxes can be used. Examples of the wax include polyolefin wax such as low molecular weight polypropylene and polyethylene, or oxidized type low molecular weight polypropylene and polyethylene, paraffin wax, synthetic ester wax, and the like. In particular, a synthetic ester wax is preferably used because of its low melting point and low viscosity. As the synthetic ester wax, it is particularly preferable to use behenyl behenate, glycerin tribehenate, pentaerythritol tetrabehenate or the like.

The content ratio of the release agent in the toner is preferably in the range of 1 mass % or more and 30 mass % or less, and more preferably in the range of 3 mass % or more and 15 mass % or less.

<Charge Control Agent>

The toner according to the present invention may further contain a charge control agent. The charge control agent used is not particularly limited as long as it is a substance capable of imparting positive or negative charge by frictional charging and is colorless, and various known positive charge control agents and negative charge control agents can be used.

The content ratio of the charge control agent in the toner is preferably in the range of 0.01 mass % or more and 30 mass % or less, and more preferably in the range of 0.1 mass % or more and 10 mass % or less.

<External Additive>

In order to improve the flowability, chargeability, cleaning property, and the like of the toner, the toner of the present invention may be formed by adding, to the toner particles, external additives such as a fluidizing agent and a cleaning aid that are so-called post-treatment agents.

Examples of the external additive include inorganic particles including inorganic oxide particles such as silica particles, alumina particles, and titanium oxide particles, inorganic stearic acid compound particles such as aluminum stearate particles and zinc stearate particles, and inorganic titanic acid compound particles such as strontium titanate particles and zinc titanate particles. These inorganic particles may be used alone or in combination of two or more.

These inorganic particles may be surface-treated with a silane coupling agent, a titanium coupling agent, a higher fatty acid, a silicone oil, or the like in order to improve heat-resistant storage stability and environmental stability.

The amount of addition of the external additive in the toner is preferably in the range of 0.05 mass % or more and 5 mass % or less, and more preferably in the range of 0.1 mass % or more and 3 mass % or less.

<Average Particle Size of Toner>

The average particle size of the toner in terms of volume-based median diameter (D50) is preferably in the range of 4 μm or more and 10 μm or less, and more preferably in the range of 6 μm or more and 9 μm or less. When the volume-based median diameter (D50) is within the above-mentioned range, the toner has high transfer efficiency, the halftone image quality is improved, and the image quality of thin lines, dots, and the like is improved.

In the present invention, the volume-based median diameter (D50) of the toner is measured and calculated using a measuring apparatus including "Coulter Counter 3" (manufactured by Beckman Coulter, Inc.) and a computer system (manufactured by Beckman Coulter, Inc.) equipped with data processing software "Software V 3.51" connected thereto.

Specifically, 0.02 g of a measurement sample (toner) is added to 20 mL of a surfactant solution (for example, a surfactant solution obtained by diluting a neutral detergent containing a surfactant component 10-fold with pure water for the purpose of dispersing toner particles) to be compatible with the solution, then the resulting mixture is ultrasonically dispersed for 1 minute to prepare a toner dispersion liquid, and the toner dispersion liquid is injected into a beaker containing "ISOTON II" (manufactured by Beckman Coulter, Inc.) in a sample stand with a pipette until the concentration displayed on the measuring apparatus reaches 8%.

Here, a concentration within the above-mentioned range provides a reproducible measurement value. Then, in the measuring apparatus, the count number of the measured particles is set to 25000, the aperture diameter is set to 50 μm, the measurement range of 1 μm or more and 30 μm or less is divided into 256 sections and the frequency values are calculated, and the particle size at 50% of volume integrated fraction from the larger side is taken as the volume-based median diameter (D50).

[Method for Producing Toner]

A method for producing the toner of the present invention is not particularly limited. For example, in the case of using only the propenimine compound as a toner, it is preferred to employ a production method including pulverizing the propenimine compound obtained by the above-mentioned synthesis method using an apparatus such as a hammer mill, a feather mill, or a counter jet mill, and then classifying the resulting particles to have a desired particle size using a dry classifier such as Spin Air Sieve, Classiel, or Micron Classifier.

In the case of producing a toner containing the propenimine compound and an additive such as a colorant but not containing a binder resin, it is preferred to employ a production method including dissolving the propenimine compound and the additive using a solvent capable of dissolving both the propenimine compound and the additive to form a solution, then removing the solvent from the solution, and then pulverizing and classifying the resulting product in the same manner as in the above-mentioned method.

In the case of producing a toner containing the propenimine compound, a binder resin, and an additive, it is preferred to employ a production method based on an emulsion aggregation method by which the particle size and shape can be easily controlled.

Such a production method preferably includes:
(1A) a binder resin particle dispersion liquid preparation step of preparing a dispersion liquid of binder resin particles;
(1B) a colorant particle dispersion liquid preparation step of preparing a dispersion liquid of colorant particles;
(1C) a propenimine compound particle dispersion liquid preparation step of preparing a dispersion liquid of propenimine compound particles;
(2) an association step of adding a flocculant to an aqueous medium in which the binder resin particles, the colorant particles, and the propenimine compound particles are present, and causing salting-out to proceed and aggregating and fusing the particles at the same time to form associated particles;
(3) an aging step of controlling the shape of the associated particles to form toner particles;
(4) a filtration and washing step of filtering out the toner particles from the aqueous medium and removing a surfactant or the like from the toner particles;
(5) a drying step of drying the washed toner particles; and
(6) an external additive adding step of adding an external additive to the dried toner particles.

Hereinafter, steps (1A) to (1C) will be described.

(1A) Binder Resin Particle Dispersion Liquid Preparation Step

In this step, resin particles are formed by conventionally known emulsion polymerization or the like, and the resin particles are aggregated and fused to form binder resin particles. In an example, polymerizable monomers forming the binder resin are charged and dispersed in an aqueous medium, and the polymerizable monomers are polymerized by a polymerization initiator to prepare a dispersion liquid of binder resin particles.

Examples of the method for obtaining the binder resin particle dispersion liquid include, in addition to the above-mentioned method, a method in which a dispersion treatment is performed in an aqueous medium without use of a solvent, and a method in which a binder resin (crystalline resin or the like) is dissolved in a solvent such as ethyl acetate to form a solution, the solution is emulsified and dispersed in an aqueous medium using a disperser, and then the solvent is removed.

In this case, the binder resin may contain a release agent (wax) in advance as necessary. In addition, it is also preferred for dispersing the binder resin particles to perform polymerization appropriately in the presence of a known surfactant (for example, an anionic surfactant such as sodium polyoxyethylene (2) dodecyl ether sulfate, sodium dodecyl sulfate, or dodecylbenzenesulfonic acid). It is also preferred to add, after mixing the surfactant, a base such as an aqueous sodium hydroxide solution in advance to the mixed liquid to adjust the pH to 9 or more and 12 or less in order to impart an aggregation property to the mixed liquid. It is also possible to prepare a release agent particle dispersion liquid separately from the binder resin particle dispersion liquid in the same manner as in the colorant particle dispersion liquid preparation step so that the release agent particle dispersion liquid may be present in the aqueous medium in the association step (2). The surfactant may also be used in preparing the colorant particle dispersion liquid or the like.

The binder resin particles in the dispersion liquid preferably have a volume-based median diameter in the range of 50 nm or more and 300 nm or less. The volume-based median diameter of the binder resin particles in the dispersion liquid can be measured by a dynamic light scattering method using "Microtrac UPA-150" (manufactured by NIKKISO CO., LTD.).

(1B) Colorant Particle Dispersion Liquid Preparation Step

The colorant particle dispersion liquid preparation step is a step of dispersing a colorant in a form of fine particles in an aqueous medium to prepare a colorant particle dispersion liquid.

The colorant can be dispersed using mechanical energy. The number-based median diameter of the colorant particles in the dispersion liquid is preferably in the range of 10 nm or more and 300 nm or less, and more preferably in the range of 50 nm or more and 200 nm or less. The number-based median diameter of the colorant particles can be measured using an electrophoretic light scattering photometer "ELS-800" (manufactured by Otsuka Electronics Co., Ltd.).

(1C) Propenimine Compound Particle Dispersion Liquid Preparation Step

The propenimine compound particle dispersion liquid preparation step is a step of dispersing the propenimine compound in a form of fine particles in an aqueous medium to prepare a dispersion liquid of the propenimine compound particles. In preparing the propenimine compound particle dispersion liquid, first, an emulsion of the propenimine compound is prepared. Examples of the method for preparing the emulsion of the propenimine compound include a method in which the propenimine compound is dissolved in an organic solvent to give a propenimine compound solution, and then the propenimine compound solution is emulsified in an aqueous medium.

The method for dissolving the propenimine compound in an organic solvent is not particularly limited, and an example thereof is a method in which the propenimine compound is added to an organic solvent and stirred and mixed so that the propenimine compound may be dissolved. The ratio of addition of the propenimine compound is preferably 5 parts by mass or more and 100 parts by mass or less, and more preferably 10 parts by mass or more and 50 parts by mass or less with respect to 100 parts by mass of the organic solvent.

Then, the propenimine compound solution and an aqueous medium are mixed and stirred using a known disperser such as a homogenizer. As a result, the propenimine compound is emulsified as droplets in the aqueous medium, so that an emulsion of the propenimine compound is prepared.

The ratio of addition of the propenimine compound solution is preferably 10 parts by mass or more and 110 parts by mass or less, and more preferably 20 parts by mass or more and 105 parts by mass or less with respect to 100 parts by mass of the aqueous medium.

The temperature of each of the propenimine compound solution and the aqueous medium at the time of mixing the propenimine compound solution and the aqueous medium is in a temperature range below the boiling point of the organic solvent, and is preferably in the range of 20° C. or more and 80° C. or less, and more preferably in the range of 30° C. or more and 75° C. or less. The temperature of the propenimine compound solution and the temperature of the aqueous medium at the time of mixing the propenimine compound solution and the aqueous medium may be the same as or different from each other, but are preferably the same as each other.

When the disperser has a capacity of, for example, 1 L or more and 3 L or less, the rotation speed of the disperser is preferably in the range of 7,000 rpm or more and 20,000 rpm or less, and the stirring time is preferably in the range of 10 minutes or more and 30 minutes or less.

The propenimine compound particle dispersion liquid is prepared by removing the organic solvent from the emulsion of the propenimine compound. Examples of the method for removing the organic solvent from the emulsion of the propenimine compound include known methods such as air blowing, heating, pressure reduction, or a combination thereof.

In an example, the emulsion of the propenimine compound is heated, for example, in an atmosphere of an inert gas such as nitrogen at preferably 25° C. or more and 90° C. or less, more preferably 30° C. or more and 80° C. or less until about 80 mass % or more and 95 mass % or less of the initial amount of the organic solvent is removed, whereby the organic solvent is removed. As a result, the organic solvent is removed from the aqueous medium so that a propenimine compound particle dispersion liquid containing the propenimine compound particles dispersed in the aqueous medium is prepared.

The mass average particle size of the propenimine compound particles in the propenimine compound particle dispersion liquid is preferably in the range of 90 nm or more and 1200 nm or less. The mass average particle size of the propenimine compound particles can be set within the above-mentioned range by appropriately adjusting the viscosity when the propenimine compound is blended in the organic solvent, the blend ratio between the propenimine compound solution and water, the stirring speed of the disperser during the preparation of the propenimine compound emulsion, and the like. The mass average particle size of the propenimine compound particles in the propenimine compound particle dispersion liquid can be measured using an electrophoretic light scattering photometer "ELS-800" (manufactured by Otsuka Electronics Co., Ltd.).

<Organic Solvent>

The organic solvent used in this step is not particularly limited as long as the solvent can dissolve the propenimine compound of the present invention. Specific examples of the organic solvent include esters such as ethyl acetate and butyl acetate, ethers such as diethyl ether, diisopropyl ether, and tetrahydrofuran, ketones such as acetone and methyl ethyl ketone, saturated hydrocarbons such as hexane and heptane, and halogenated hydrocarbons such as dichloromethane, dichloroethane, and carbon tetrachloride.

These organic solvents may be used alone or in combination of two or more. Among these organic solvents, ketones and halogenated hydrocarbons are preferred, and methyl ethyl ketone and dichloromethane are more preferred.

<Aqueous Medium>

Examples of the aqueous medium used in this step include water, and aqueous media containing water as a main component and containing optional components such as water-soluble solvents including alcohols and glycols, surfactants, and dispersants. The aqueous medium used is preferably a mixture of water and a surfactant.

Examples of the surfactant include cationic surfactants, anionic surfactants, and nonionic surfactants. Examples of the cationic surfactant include dodecylammonium chloride, dodecylammonium bromide, dodecyltrimethylammonium bromide, dodecylpyridinium chloride, dodecylpyridinium bromide, and hexadecyltrimethylammonium bromide. Examples of the anionic surfactant include fatty acid soaps such as sodium stearate and sodium dodecanoate, sodium dodecylbenzenesulfonate, and sodium dodecyl sulfate. Examples of the nonionic surfactant include polyoxyethylene dodecyl ether, polyoxyethylene hexadecyl ether, polyoxyethylene nonylphenyl ether, polyoxyethylene lauryl ether, polyoxyethylene sorbitan monooleate ether, and monodecanoyl sucrose.

These surfactants may be used alone or in combination of two or more. Among the surfactants, anionic surfactants are preferably used, and sodium dodecylbenzenesulfonate is more preferably used.

The amount of addition of the surfactant is preferably 0.01 part by mass or more and 10 parts by mass or less, and more preferably 0.04 part by mass or more and 1 part by mass or less based on 100 parts by mass of the aqueous medium.

The steps from the association step (2) to the external additive adding step (6) can be performed according to various conventionally known methods.

The flocculant used in the association step (2) is not particularly limited, but a flocculant selected from metal salts is suitably used. Examples of the metal salt include monovalent metal salts such as salts of alkali metals including sodium, potassium, and lithium; divalent metal salts such as salts of calcium, magnesium, manganese, and copper; and trivalent metal salts such as salts of iron and aluminum. Specific examples of the metal salt include sodium chloride, potassium chloride, lithium chloride, calcium chloride, magnesium chloride, zinc chloride, copper sulfate, magnesium sulfate, and manganese sulfate. Among these, it is particularly preferred to use a divalent metal salt because the aggregation can proceed with a smaller amount of the salt. These salts may be used alone or in combination of two or more.

[Developer]

It is conceivable that the toner of the present invention will be used, for example, as a one-component magnetic toner containing a magnetic material, a two-component developer containing a mixture of the toner and a so-called carrier, or a nonmagnetic toner by itself, and any of them can be suitably used.

As for the magnetic material, for example, magnetite, γ-hematite, various ferrites, or the like can be used.

As for the carrier that is a component of the two-component developer, it is possible to use magnetic particles made of a conventionally known material such as metals including iron, steel, nickel, cobalt, ferrite, and magnetite, and alloys of these metals with a metal such as aluminum or lead.

As for the carrier, it is preferred to use a coated carrier obtained by coating the surface of magnetic particles with a coating agent such as a resin, or a so-called resin dispersion type carrier obtained by dispersing a magnetic material powder in a binder resin. The coating resin is not particularly limited, and for example, an olefin resin, a styrene resin, a styrene acrylic resin, a silicone resin, a polyester resin, a fluororesin, or the like is used. In addition, the resin for forming the resin dispersion type carrier is not particularly limited, and a known resin can be used. For example, an acrylic resin, a styrene acrylic resin, a polyester resin, a fluororesin, a phenol resin, and the like can be used.

The volume-based median diameter of the carrier is preferably in the range of 20 μm or more and 100 μm or less, and more preferably in the range of 25 μm or more and 80 μm or less. The volume-based median diameter of the carrier can be typically measured by a laser diffraction type particle size distribution analyzer "HELOS" (manufactured by Sympatec GmbH) equipped with a wet disperser.

The mixed amount of the toner with respect to the carrier is preferably in the range of 2 mass % or more and 10 mass % or less based on 100 mass % in total of the toner and the carrier.

[Image Forming Method]

The toner of the present invention can be used in various known electrophotographic image forming methods. For example, the toner can be used in a monochrome image forming method or a full-color image forming method. The full-color image forming method can be applied to any image forming method such as a four-cycle image forming method in which four types of color developing devices for yellow, magenta, cyan, and black, and one photoreceptor are used, and a tandem image forming method in which an image forming unit is provided for each color, the image forming unit including a color developing device and a photoreceptor for each color.

An image forming method according to an embodiment of the present invention is an image forming method including a step of fixing an image by light irradiation, and preferably includes steps of forming an image on a recording medium using the toner containing the propenimine compound of the present invention, irradiating the image formed on the recording medium with light in a wavelength region preferably in the range of 280 nm or more and 420 nm or less, more preferably in the range of 300 nm or more and 400 nm or less, and still more preferably in the range of 330 nm or more and 390 nm or less, and fixing the image. The reason why light in a wavelength region of 280 nm or more and 420 nm or less is used in the step of irradiating the image with light is that it is suitable in that the compound well absorbs light mainly in the ultraviolet region, the light melting property can be improved, the propenimine compound in the toner can be sufficiently fluidized, and the image (toner image) on the recording medium can be quickly softened. If the applied light has a wavelength shorter than 280 nm, the energy increases, and the propenimine compound may be decomposed. Meanwhile, if the applied light has a wavelength longer than 420 nm, the propenimine compound having no absorption region on the long wavelength side may not be fluidized. From the viewpoint of obtaining better fixability, the step of fixing the image on the recording medium preferably includes a step of pressurizing, with a pressurizing member, the recording medium on which the image is formed. Further, from the viewpoint of obtaining better fixability, the pressurizing member preferably has a temperature of 30° C. or more and 100° C. or less.

FIG. 1 is a schematic configuration diagram illustrating an image forming apparatus 100 used in an image forming method according to an embodiment of the present invention. The image forming apparatus used in the present invention is not limited to the following embodiment and the illustrated example. FIG. 1 illustrates an example of a monochrome image forming apparatus 100, but the present invention can also be applied to a color image forming apparatus.

The image forming apparatus 100 is an apparatus that forms an image on a recording sheet S as a recording medium. The image forming apparatus 100 includes an image reading device 71 and an automatic document feeder 72, and forms an image on the recording sheet S conveyed by a sheet conveying system 7 through the use of an image forming unit 10, an irradiation unit 40, and a pressure-bonding unit 9.

The recording medium used in the image forming apparatus 100 is the recording sheet S, but the medium to be subjected to image formation may be other than a paper sheet.

A document d placed on a document table of the automatic document feeder 72 is scanned and exposed by an optical system of a scanning exposure device in the image reading device 71, and read by an image sensor CCD. An analog signal obtained by photoelectric conversion at the image sensor CCD is subjected to analog processing, A/D conversion, shading correction, image compression processing, and the like in an image processing unit 20, and then input to an exposure device 3 in the image forming unit 10.

The sheet conveying system 7 includes a plurality of trays 16, a plurality of sheet feeders 11, conveying rollers 12, a conveying belt 13, and the like. Each of the trays 16 stores recording sheets S of a predetermined size, and the sheet feeder 11 of the tray 16 determined in accordance with an instruction from a control unit 90 is operated to supply a recording sheet S. The conveying rollers 12 convey the recording sheet S fed from the tray 16 by the sheet feeder 11 or the recording sheet S fed from a manual sheet feeder 15 to the image forming unit 10.

The image forming unit 10 has a configuration in which around a photoreceptor 1 and in a rotation direction of the photoreceptor 1, a charger 2, an exposure device 3, a developing unit 4, a transfer unit 5, a static elimination unit 6, and a cleaning unit 8 are arranged in this order.

The photoreceptor 1 as an image carrier is an image carrier having a photoconductive layer formed on a surface thereof, and is configured to be rotatable in a direction of an arrow in FIG. 1 by a driving device (not illustrated). A thermo-hygrometer 17 that detects the temperature and humidity in the image forming apparatus 100 is provided in the vicinity of the photoreceptor 1.

The charger 2 uniformly impart charges to the surface of the photoreceptor 1 to uniformly charge the surface of the photoreceptor 1. The exposure device 3 includes a beam emission source such as a laser diode, and irradiates the charged surface of the photoreceptor 1 with beam light to dissipate the charges of the irradiated portion, and forms an electrostatic latent image corresponding to image data on the photoreceptor 1. The developing unit 4 supplies a toner contained therein to the photoreceptor 1 to form a toner image based on the electrostatic latent image on the surface of the photoreceptor 1.

The transfer unit 5 faces the photoreceptor 1 with the recording sheet S interposed therebetween, and transfers the toner image to the recording sheet S. The static elimination unit removes static electricity on the photoreceptor 1 after the toner image is transferred. The cleaning unit 8 includes a blade 85. The blade 85 cleans the surface of the photoreceptor 1 to remove the developer remaining on the surface of the photoreceptor 1.

The recording sheet S to which the toner image has been transferred is irradiated with light by the irradiation unit 40 while being conveyed by the conveying belt 13, and then conveyed to the pressure-bonding unit 9. The pressure-bonding unit 9 is optionally installed, and applies only pressure or heat and pressure to the recording sheet S to which the toner image has been transferred by pressurizing members 91 and 92 to perform fixing processing, thereby fixing the image on the recording sheet S. The recording sheet S on which the image is fixed is conveyed to a sheet ejector 14 by the conveying rollers, and is ejected from the sheet ejector 14 to the outside of the apparatus.

In addition, the image forming apparatus 100 includes a sheet reversing unit 24, and it is possible to convey the recording sheet S having been subjected to the heat fixing processing to the sheet reversing unit 24 before the sheet ejector 14 and eject the recording sheet S with the front and back reversed, or to convey the recording sheet S with the front and back reversed to the image forming unit 10 again and form an image on both sides of the recording sheet S.

<Irradiation Unit>

Figure 2:
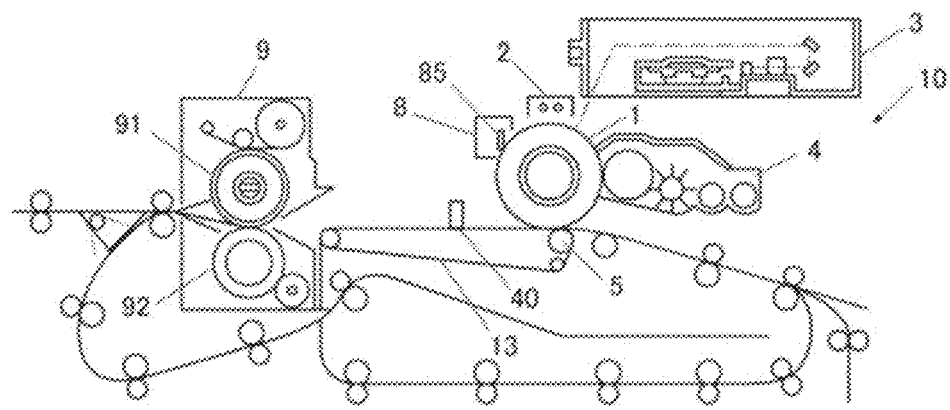
FIG. 2 is a schematic cross-sectional view illustrating a fixing device including the irradiation unit in the image forming apparatus according to the embodiment of the present invention.

FIG. 2 is a schematic configuration diagram of the irradiation unit 40 in the image forming apparatus 100.

The image forming apparatus 100 according to an embodiment of the present invention includes, above the conveying belt 13 and between the transfer unit 5 and the pressure-bonding unit 9, the irradiation unit 40 that can irradiate, with light, the toner image on the recording sheet S conveyed by the conveying belt 13 under appropriate irradiation conditions. Examples of a device that constitutes the irradiation unit 40 include a light emitting diode (LED) and a laser light source. As for the irradiation unit 40, it is possible to use, for example, a scanning type irradiation unit 40 capable of irradiating the entire toner image in a short time by scanning and exposing (irradiating with light) the toner image on the recording sheet at (ultra) high speed. Alternatively, the irradiation unit 40 may also be a fixed irradiation unit 40 in which a large number of light sources are arranged in a horizontal line (in a direction perpendicular to the conveyance direction) or arranged vertically and horizontally without a gap so that the entire toner image on the recording sheet can be irradiated with light at a time. The light irradiation technique is not particularly limited, and a conventionally known technique can be applied.

The irradiation unit 40 melts and fluidizes, by light irradiation, the propenimine compound of the present invention contained in the toner in the toner image. The wavelength of the light applied by the irradiation unit 40 may be any wavelength as long as the light can sufficiently fluidize the propenimine compound, and the light is ultraviolet light preferably having a wavelength in the range of 280 nm or more and 420 nm or less, more preferably in the range of 300 nm or more and 400 nm or less, and still more preferably in the range of 330 nm or more and 390 nm or less. When the wavelength of the light applied by the irradiation unit 40 is within the above-mentioned range, the compound well absorbs light in the ultraviolet region and has improved light melting property, and a toner containing the compound has improved fixability. Further, when the compound is irradiated with the irradiation light having the above-mentioned wavelength, it is possible to fluidize the compound without applying heat or pressure. Therefore, introduction of the propenimine compound into a toner provides a toner that can be fixed at the above-mentioned wavelength and has high color reproducibility. The light irradiation amount in the irradiation unit 40 may be any amount as long as the propenimine compound of the present invention can be sufficiently melted and fluidized, and is preferably in the range of 0.1 J/cm$^2$ or more and 200 J/cm$^2$ or less, more preferably in the range of 0.5 J/cm$^2$ or more and 100 J/cm$^2$ or less, and still more preferably in the range of 1.0 J/cm$^2$ or more and 50 J/cm$^2$ or less. When the light irradiation amount corresponds to an energy of 0.1 J/cm$^2$ or more, a reaction of E→Z (fluidization) occurs beyond the energy barrier, and the propenimine compound has improved light melting property, so that the compound can be fluidized. Meanwhile, when the light irradiation amount is 200 J/cm$^2$ or less, the energy is not too large, and the propenimine compound can be satisfactorily fluidized without being broken.

In order to non-fluidize the propenimine compound of the present invention contained in the toner in the image, it is preferred to leave the propenimine compound at room temperature (without heating; 25±15° C.) without applying external energy or external force such as light irradiation, heating, and pressurization. Specifically, after the sheet is passed through the fixing unit 9 as necessary, the sheet may be ejected by conveyance as it is and left at room temperature.

The following light irradiation may also be performed at the time of non-fluidizing the propenimine compound. A light irradiation unit (not illustrated) for non-fluidizing the propenimine compound is preferably provided on the downstream side of the irradiation unit 40. When the fixing unit 9 is provided, it is preferred to provide an irradiation unit above the conveying belt on the downstream side of the fixing unit 9. The wavelength of the irradiation light at the time of non-fluidizing the propenimine compound is only required to be capable of sufficiently non-fluidizing and solidifying the propenimine compound, but it is preferred that the irradiation light have a wavelength longer than that of the irradiation light at the time of fluidizing the propenimine compound. For example, the wavelength is in the range of 400 nm or more and 800 nm or less, preferably in the range of 420 nm or more and 800 nm or less, and more preferably in the range of 430 nm or more and 730 nm or less. At a wavelength of 800 nm or less, heat is not generated because the light is not in the infrared region, heat loss due to photothermal conversion is prevented, and irradiation energy is efficiently provided to the photoisomerization reaction. At a wavelength of 400 nm or more, since the light is not in the ultraviolet region, the propenimine compound is appropriately non-fluidized without being fluidized. From these facts, the best wavelength region is in the range of 450 nm or more and 650 nm or less. When the wavelength is within the above-mentioned range, the compound well absorbs light in the visible light region and has improved photocurability, and a toner containing the compound has improved fixability. Further, when the compound is irradiated with light having the above-mentioned wavelength, it is possible to non-fluidize the compound without applying heat or pressure. Therefore, introduction of the propenimine compound into a toner makes it possible to solidify a toner image on a recording sheet more reliably, further improve the fixability of the toner image to the recording sheet, and provide a toner having high color reproducibility. The light irradiation amount in the irradiation unit may be any amount as long as the propenimine compound of the present invention, which undergoes phase transition by light absorption and is contained in the toner in a developer, can be sufficiently non-fluidized (solidified), and is preferably in the range of 0.1 J/cm$^2$ or more and 200 J/cm$^2$ or less, more preferably in the range of 0.5 J/cm$^2$ or more and 100 J/cm$^2$ or less, and still more preferably in the range of 1.0 J/cm$^2$ or more and 50 J/cm$^2$ or less. When the light irradiation amount corresponds to an energy of 0.1 J/cm$^2$ or more, a reaction of Z→E (non-fluidization) occurs beyond the energy barrier, so that the propenimine compound can be non-fluidized. Meanwhile, when the light irradiation amount is 200 J/cm$^2$ or less, the energy is not too large, and the propenimine compound can be satisfactorily non-fluidized (solidified) without being broken.

That is, an image forming method according to an embodiment of the present invention is an image forming method including a step of fixing an image by light irradiation, and includes steps of forming an image on a recording medium using the toner containing the propenimine compound, irradiating the image formed on the recording medium with light in a wavelength region of 280 nm or more and 420 nm or less, and fixing the image on the recording medium. If necessary, the step of fixing the image on the recording medium includes a step of irradiating the softened image with light in a wavelength region of 400 nm or more and 800 nm or less to solidify the image. Note that the step of fixing the image preferably further includes a step of pressurizing the softened image. In the pressurizing step, it is preferred to further heat the softened image at 30° C. or more and 100° C. or less. This is because heating can further soften the image.

The irradiation unit 40 and the optional irradiation unit (not illustrated) for non-fluidization apply light to a first surface of the recording sheet S, which is on the photoreceptor side and holds the image (toner image), and are disposed on the photoreceptor side with respect to the surface of the recording sheet S nipped between the photoreceptor 1 and a transfer roller 50. Further, the irradiation unit 40 and the optional irradiation unit are arranged in this order in the conveyance direction of the recording sheet S.

The irradiation unit 40 is disposed on the downstream side in the sheet conveyance direction with respect to the nip position between the photoreceptor 1 and the transfer roller 50 and on the upstream side in the sheet conveyance direction with respect to the pressure-bonding unit 9.

The optional irradiation unit is installed on the downstream side in the sheet conveyance direction with respect to the irradiation unit 40 and on the upstream side in the sheet conveyance direction with respect to the sheet ejector 14. The optional irradiation unit can be installed between the pressure-bonding unit 9 and the sheet ejector 14 in the sheet conveyance direction.

According to the image forming method of the embodiment of the present invention, after the photoreceptor 1 is charged by application of a uniform potential from the charger 2, the photoreceptor 1 is scanned with a light flux emitted by the exposure device 3 based on original image data, whereby an electrostatic latent image is formed. Then, the developing unit 4 supplies, onto the photoreceptor 1, a developer that contains the toner containing the propenimine compound of the present invention.

When a recording sheet S is conveyed from any of the trays 16 to the image forming unit 10 in accordance with the position timing of the transfer member 50 by the rotation of the photoreceptor 1, the toner image on the photoreceptor 1 is transferred to the recording sheet S nipped between the transfer member 50 and the photoreceptor 1 by the transfer bias applied to the transfer member 50.

The transfer member 50 also serves as a pressurizing member, and can reliably bring the propenimine compound contained in the toner image into close contact with the recording sheet S while transferring the toner image from the photoreceptor 1 to the recording sheet S.

After the toner image is transferred to the recording sheet S, the blade 85 of the cleaning unit 8 removes the developer remaining on the surface of the photoreceptor 1.

In a process in which the recording sheet S to which the toner image has been transferred is conveyed to the pressure-bonding unit 9 by the conveying belt 13, the irradiation unit 40 irradiates the toner image (image) transferred to the recording sheet S with light in a wavelength region of 280 nm or more and 420 nm or less. Since the toner image on the first surface of the recording sheet S is irradiated with the light in the above-mentioned wavelength region by the irradiation unit 40, the image can be more reliably melted, and the fixability of the toner image to the recording sheet S can be improved.

When the recording sheet S holding the image is conveyed by the conveying belt 13 and reaches the pressure-bonding unit 9, the pressurizing members 91 and 92 pressure-bond the image to the first surface of the recording sheet S. Since the image has been softened by the light applied from the irradiation unit 40 before being fixed by the pressure-bonding unit 9, energy for pressure-bonding the image to the recording sheet S can be saved. That is, the image forming method of the present invention preferably further includes a step of pressurizing the softened image with a pressurizing member before solidifying the image and fixing the image on the recording medium. Application of pressure by the pressurizing members 91 and 92 further improves fixability of the image to the recording sheet S. The pressurizing members 91 and 92 preferably have a roller shape.

The pressure at the time of pressurizing the image on the recording medium is not particularly limited, but is preferably 0.01 MPa or more and 5.0 MPa or less, and more preferably 0.05 MPa or more and 1.0 MPa or less. When the pressure is 0.01 MPa or more, the image can be largely deformed, so that the contact area between the image and the recording sheet S is increased, and the image fixability can be further improved easily. In addition, when the pressure is 5.0 MPa or less, shock noise at the time of pressurization can be reduced.

Further, the pressurizing member 91 can heat the image on the recording sheet S when the recording sheet S passes between the pressurizing members 91 and 92. The heating further improves fixability of the image softened by the light irradiation to the recording sheet S. The temperature of the pressurizing member 91 when heating the image is preferably 30° C. or more and 100° C. or less, and more preferably 40° C. or more and 100° C. or less. The pressurizing member 91 used as a heating member may be either of a contact type or a non-contact type as long as it is a member capable of heating the toner, but a non-contact type heating member is preferred.

It is preferred that the recording sheet S having passed between the pressurizing members 91 and 92 be left at room temperature without being subjected to non-fluidization by a non-fluidizing means before reaching the sheet ejector 14. When the recording sheet S is left at room temperature before reaching the sheet ejector 14, the image on the recording sheet S can be reliably solidified, and the fixability of the image to the recording sheet S can be further improved. However, it is possible to provide, as necessary, the optional irradiation unit for irradiating the image on the recording sheet S with visible light in a wavelength region of 400 nm or more and 800 nm or less. Also by irradiating the image on the recording sheet S with visible light in the above-mentioned wavelength region from the optional irradiation unit, the image can be reliably solidified, and the fixability of the image to the recording sheet S can be improved.

In the image forming method of the present invention, the pressure-bonding unit 9 in FIG. 2 is not necessarily provided. That is, it is not necessary to pressure-bond and heat the image formed on the recording medium after the image is irradiated with light in the above-mentioned wavelength region from the irradiation unit 40 and softened. As described above, it is preferred that the recording sheet S be left at room temperature without being subjected to non-fluidization by a non-fluidizing means before reaching the sheet ejector 14. However, it is also possible to irradiate the softened image with visible light in the above-mentioned wavelength region from the optional irradiation unit without pressure-bonding and heating the image to solidify and fix (anchor) the image to the recording medium.

When forming images on both sides of the recording sheet S, it is preferred to convey the recording sheet S having been subjected to pressure-bonding to the sheet reversing unit 24 before the sheet ejector 14, and eject the recording sheet S with the front and back reversed, or to convey the recording sheet S with the front and back reversed to the image forming unit 10 again.

(Photoresponsive Adhesive)

Since the propenimine compound of the present invention is fluidized by light irradiation and reversibly non-fluidized, the propenimine compound can be applied to a photoresponsive adhesive that can be repeatedly used. For example, the propenimine compound can be applied to various adhesion techniques as an adhesive that is capable of repeated desorption and adhesion in response to a change in viscosity (friction coefficient), the repetition including desorption (fluidization) by light irradiation and adhesion (non-fluidization) by natural environment (leaving at room temperature).

The photoresponsive adhesive of the present invention can be used in temporary fixing for which the adhesive can be repeatedly used, and is also suitable for recycling use, but the use is not limited thereto.

(Optical Switching Material)

Since the propenimine compound of the present invention is fluidized by light irradiation and reversibly non-fluidized, the propenimine compound can be applied to an optical switching material. The optical switching material can be produced, for example, by utilizing a change in color or polarity, mass transfer, a change in orientation, a change in viscosity, a change in surface tension, or the like due to photoisomerization. For example, in a liquid crystal material or the like, the propenimine compound can be applied to pattern drawing in which patterns can be repeatedly redrawn in response to a change in molecular orientation due to photoisomerization. In addition, for example, the surface of a polymer film can be finely processed by using a change in surface tension due to light irradiation or mass transfer caused by such change. That is, an embodiment of the present invention is an optical switching material containing the propenimine compound of the present invention. For example, the propenimine compound of the embodiment can be used as an optical switching material as it is or with the addition of an appropriate amount of an arbitrary known additive.

The optical switching material of the present invention can be used in a liquid crystal display material or surface processing of a polymer film, but the use is not limited thereto.

EXAMPLES

Effects of the present invention will be described with reference to the following examples and comparative examples. However, the technical scope of the present invention is not limited only to the following examples.
[Synthesis of Propenimine Compound]
(Synthesis of Compound No. 5)

[Chemical Formula 5]

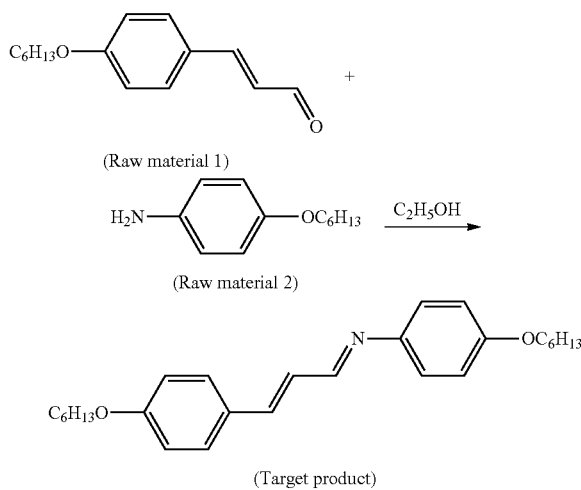

(Raw material 1)

(Raw material 2)

(Target product)

To a 50-mL four-necked flask equipped with a condenser and a thermometer, 3-(4-(hexyloxy)phenyl)acetylaldehyde (5.00 g, 21.5 mmol) (raw material 1), 4-hexyloxyaniline (4.16 g, 21.5 mmol) (raw material 2), and 20 mL of ethanol were added and stirred. The resulting mixture was refluxed for 5 hours at an internal temperature of 77° C. or more and 78° C. or less.

It was confirmed by thin layer chromatography (TLC) that 4-hexyloxyaniline had disappeared, and after the internal temperature was lowered to room temperature, the reaction liquid was added to 200 mL of water to stop the reaction. The target product was extracted with ethyl acetate and washed with water. The resulting ethyl acetate extract was dried and then concentrated to give crude crystals of Compound No. 5. The crude crystals were recrystallized from ethanol to give 8.07 g of Compound No. 5 as the target product (yield: 92%).

$^1$H-NMR (CDCl$_3$, 400 MHz) δ (ppm); 8.70 (S, 1H), 7.22 (D, 1H), 6.85 (D, 1H), 6.96 (D, 2H), 7.68 (D, 2H), 7.39 (D, 2H), 7.01 (D, 2H), 6.96 (D, 2H), 4.11 (T, 4H), 1.80 (M, 4H), 1.47 to 1.37 (M, 12H), 0.89 (T, 6H).
(Synthesis of Compound Nos. 1 to 4 and 6 to 57)

Compound Nos. 1 to 4 and 6 to 57 as target products were synthesized in the same manner as in the synthesis of Compound No. 5 except that 3-(4-(hexyloxy)phenyl)acetylaldehyde (raw material 1) and 4-hexyloxyaniline (raw material 2) were respectively changed to an acetylaldehyde compound (raw material 1) and an aniline compound (raw material 2) shown in Tables 2-1 to 2-3.

Production of compounds was confirmed by $^1$H-NMR in the same manner as in Compound No. 5, and it was found that the target Compound Nos. 1 to 4 and 6 to 57 were obtained. $^1$H-NMR spectra of some compounds among the target compounds are shown below.
•Compound No. 3
$^1$H-NMR (CDCl$_3$, 400 MHz) δ (ppm); 7.68 (M, 2H), 7.64 (S, 1H), 7.26 (D, 2H), 7.22 (D, 2H), 7.01 (M, 2H), 4.11 (M, 2H), 2.65 (M, 2H), 2.07 (S, 3H), 1.26 to 1.47 (M, 6H), 1.33 to 1.74 (M, 20H), 0.89 (T, 6H).
•Compound No. 7
$^1$H-NMR (CDCl$_3$, 400 MHz) δ (Ppm); 8.70 (S, 1H), 7.59 (D, 2H), 7.26 (D, 2H), 6.22 (D, 2H), 7.01 (D, 2H), 6.34 (S, 1H), 4.11 (T, 2H), 2.64 (T, 2H), 2.44 (M, 2H), 1.74 (M, 2H), 1.63 (M, 2H), 1.43 (M, 2H), 1.26 to 1.29 (M, 30H), 1.07 (T, 3H), 0.89 (T, 6H).
•Compound No. 10
$^1$H-NMR (CDCl$_3$, 400 MHz) δ (ppm); 8.7 (S, 1H), 7.39 (D, 2H), 7.10 (S, 2H), 6.96 (D, 2H), 6.78 (S, 1H), 5.36 (S, 1H), 4.11 (T, 2H), 2.64 (T, 4H), 2.12 (S, 3H), 1.77 (M, 2H), 1.39 (M, 4H), 1.26 to 1.29 (M, 10H), 0.89 to 0.90 (M, 9H).
•Compound No. 14
$^1$H-NMR (CDCl$_3$, 400 MHz) δ (ppm); 8.7 (S, 1H), 8.19 (S, 1H), 7.64 (D, 2H), 7.29 (D, 1H), 7.22 (D, 1H), 7.05 (D, 1H), 6.85 (D, 1H), 6.77 (D, 2H), 4.11 (T, 2H), 1.80 (M, 2H), 1.58 (M, 2H), 1.47 (M, 2H), 1.29 to 1.37 (M, 12H), 0.89 (T, 6H).
•Compound No. 22
$^1$H-NMR (CDCl$_3$, 400 MHz) δ (ppm); 8.70 (S, 1H), 7.93 (S, 1H), 7.52 (D, 1H), 7.19 to 7.20 (M, 2H), 7.09 (T, 1H), 6.73 to 6.75 (M, 2H), 5.36 (S, 1H), 4.11 (T, 2H), 2.64 (T, 2H), 2.12 (S, 3H), 1.80 (M, 2H), 1.56 (M, 2H), 1.42 (M, 2H), 1.26 to 1.33 (M, 16H), 0.89 (T, 6H).
•Compound No. 23
$^1$H-NMR (CDCl$_3$, 400 MHz) δ (ppm); 8.7 (S, 1H), 7.68 (D, 2H), 7.22 (D, 2H), 7.01 (D, 2H), 6.85 (D, 1H), 6.26 (S, 2H), 4.11 (T, 6H), 1.74 (M, 6H), 1.43 to 1.47 (M, 6H), 1.26 to 1.29 (M, 10H), 0.96 (T, 6H), 0.89 (T, 3H).
•Compound No. 27
$^1$H-NMR (CDCl$_3$, 400 MHz) δ (ppm); 8.70 (S, 1H), 7.39 (D, 2H), 7.08 (D, 1H), 6.96 (D, 2H), 6.85 (D, 1H), 6.67 (D, 1H), 6.65 (M, 1H), 4.11 (T, 2H), 2.44 (S, 3H), 1.88 (M, 2H), 1.47 (M, 2H), 1.37 (M, 4H), 0.89 (T, 3H).
•Compound No. 29
$^1$H-NMR (CDCl$_3$, 400 MHz) δ (ppm); 7.66 (S, 1H), 7.39 (D, 2H), 6.90 to 6.96 (M, 4H), 4.11 (T, 2H), 2.76 (M, 2H), 2.07 (S, 3H), 1.80 (M, 2H), 1.37 to 1.47 (M, 6H), 1.18 (T, 3H), 0.89 (T, 3H).
•Compound No. 31
$^1$H-NMR (CDCl$_3$, 400 MHz) δ (ppm); 8.70 (S, 1H), 7.74 (D, 1H), 7.39 (D, 2H), 6.95 to 6.96 (T, 3H), 6.85 (D, 1H), 6.72 (D, 1H), 6.50 (T, 1H), 4.11 (T, 2H), 1.80 (M, 2H), 1.47 (M, 2H), 1.37 (M, 4H), 0.89 (T, 3H).
•Compound No. 34
$^1$H-NMR (CDCl$_3$, 400 MHz) δ (ppm); 8.15 (S, 1H), 7.25 (D, 1H), 6.95 (D, 1H), 6.75 to 6.8 (M, 4H), 4.11 (T, 2H), 2.34 (S, 6H), 2.07 (S, 3H), 1.77 (M, 2H), 1.39 (M, 4H), 0.90 (T, 3H).
•Compound No. 35
$^1$H-NMR (CDCl$_3$, 400 MHz) δ (ppm); 9.40 (S, 1H), 8.7 (S, 1H), 7.39 (D, 2H), 6.96 (D, 2H), 6.85 (D, 1H), 6.72 (D, 1H), 6.37 (D, 1H), 5.73 (D, 1H), 4.11 (T, 2H), 2.29 (S, 3H), 1.74 (M, 2H), 1.43 (M, 2H), 1.26 to 1.29 (M, 5H), 0.89 (T, 3H).

•Compound No. 37
 ¹H-NMR (CDCl₃, 400 MHz) δ (ppm); 8.7 (S, 1H), 7.39 (D, 2H), 7.15 (D, 1H), 6.96 (D, 2H), 6.85 (D, 1H), 6.72 (D, 1H), 6.64 (D, 1H), 6.07 (T, 1H), 4.11 (T, 2H), 3.91 (S, 3H), 1.80 (M, 2H), 1.47 (T, 2H), 1.37 (M, 4H), 0.89 (T, 3H).

•Compound No. 39
 ¹H-NMR (CDCl₃, 400 MHz) δ (ppm); 8.7 (S, 1H), 7.22 to 7.26 (M, 4H), 6.85 (D, 1H), 6.79 (D, 1H), 6.41 (S, 1H), 5.85 (S, 1H), 3.60 (S, 3H), 2.64 (T, 2H), 2.19 (S, 3H), 1.63 (T, 2H), 1.26 (M, 16H), 0.89 (T, 3H).

•Compound No. 41
 ¹H-NMR (CDCl₃, 400 MHz) δ (ppm); 8.7 (S, 1H), 7.59 (D, 2H), 7.35 (D, 1H), 7.01 (D, 2H), 6.64 to 6.67 (M, 2H), 4.11 (T, 2H), 2.44 (S, 3H), 2.14 (S, 3H), 1.74 (M, 2H), 1.43 (M, 2H), 1.26 to 1.30 (M, 8H), 0.89 (T, 3H).

•Compound No. 44
 ¹H-NMR (CDCl₃, 400 MHz) δ (ppm); 8.7 (S, 1H), 7.68 (D, 2H), 7.44 (D, 1H), 7.22 (D, 1H), 7.01 (D, 2H), 6.85 (D, 1H), 6.35 to 6.38 (M, 2H), 4.11 (T, 2H), 1.80 (M, 2H), 1.47 (M, 2H), 1.37 (M, 4H), 0.89 (T, 3H).

•Compound No. 46
 ¹H-NMR (CDCl₃, 400 MHz) δ (ppm); 8.7 (S, 1H), 7.29 (D, 1H), 7.16 (D, 1H), 6.92 (D, 2H), 6.77 (D, 2H), 5.36 (S, 1H), 2.71 (M, 2H), 2.64 (M, 2H), 2.12 (S, 3H), 1.63 (T, 2H), 1.26 (M, 12H), 1.18 (M, 3H), 0.89 (T, 3H).

•Compound No. 49
 ¹H-NMR (CDCl₃, 400 MHz) δ (ppm); 8.7 (S, 1H), 7.59 to 7.60 (D, 3H), 7.01 (D, 2H), 6.34 (S, 1H), 6.06 (D, 1H), 5.88 (D, 1H), 4.11 (T, 2H), 2.44 (M, 2H), 2.29 (S, 3H), 1.77 (M, 2H), 1.39 (M, 4H), 1.07 (M, 3H), 0.90 (T, 3H).

•Compound No. 51
 ¹H-NMR (CDCl₃, 400 MHz) δ (ppm); 8.7 (S, 1H), 7.68 (D, 2H), 7.22 (D, 2H), 7.01 (D, 2H), 6.85 (D, 2H), 6.05 (D, 1H), 5.94 (D, 1H), 4.24 (M, 2H), 4.11 (T, 2H), 2.19 (S, 3H), 1.80 (M, 2H), 1.47 (M, 2H), 1.33 (M, 4H), 1.06 (M, 3H), 0.89 (T, 3H).

•Compound No. 53
 ¹H-NMR (CDCl₃, 400 MHz) δ (ppm); 8.7 (S, 1H), 7.59 (D, 2H), 7.01 (D, 2H), 6.34 (D, 2H), 5.98 (D, 1H), 4.11 (T, 2H), 3.60 (S, 3H), 2.44 (M, 2H), 2.09 (S, 3H), 1.74 (M, 2H), 1.43 (M, 2H), 1.26 (M, 26H), 1.07 (T, 3H), 0.89 (T, 3H).

•Compound No. 54
 ¹H-NMR (CDCl₃, 400 MHz) δ (ppm); 8.7 (S, 1H), 7.62 (M, 1H), 7.39 (D, 2H), 7.09 to 7.29 (M, 3H), 6.96 (D, 2H), 6.85 (D, 1H), 6.72 (D, 1H), 6.5 (S, 1H), 4.11 (T, 2H), 3.99 (S, 3H), 1.80 (M, 2H), 1.4 (M, 6H), 0.9 (T, 3H).

•Compound No. 56
 ¹H-NMR (CDCl₃, 400 MHz) δ (ppm); 8.7 (S, 1H), 7.39 (D, 2H), 7.0 (M, 3H), 6.85 (D, 1H), 6.72 (D, 1H), 4.1 (T, 2H), 2.6 (M, 2H), 1.8 (M, 2H), 1.3 to 1.5 (M, 9H), 0.9 (T, 3H).

TABLE 2-1

| Compound No. | Raw material 1 | Raw material 2 |
|---|---|---|
| 1 | $C_4H_9$—C₆H₄—CH=CH—CH=O | $H_2N$—C₆H₄—$C_5H_{11}$ |
| 2 | $C_6H_{13}$—C₆H₄—CH=CH—CH=O | $H_2N$—C₆H₄—$OC_6H_{13}$ |
| 3 | $C_{10}H_{21}$—C₆H₄—CH=CH—C(CH₃)=O | $H_2N$—C₆H₄—$C_4H_9$ |
| 4 | $C_4H_9O$—C₆H₄—CH=CH—CH=O | $H_2N$—C₆H₄—$C_8H_{17}$ |
| 5 | $C_6H_{13}O$—C₆H₄—CH=CH—CH=O | $H_2N$—C₆H₄—$OC_6H_{13}$ |
| 6 | $C_6H_{13}O$—C₆H₄—CH=CH—CH=O | $H_2N$—3,5-($C_2H_5$)₂-C₆H₃ |
| 7 | $C_{11}H_{23}O$—C₆H₄—C(CH=)(C₂H₅)—CH=O | $H_2N$—C₆H₄—$C_{10}H_{21}$ |

TABLE 2-1-continued

| Compound No. | Raw material 1 | Raw material 2 |
|---|---|---|
| 8 | 4-$C_5H_{11}$, 2-$C_4H_9$-phenyl-CH=CH-CH=O | $H_2N$-phenyl-$OC_4H_9$ (para) |
| 9 | 4-$C_7H_{15}$, 3-$C_7H_{15}$-phenyl-CH=CH-CH=O | $H_2N$-phenyl with 3-$C_7H_{15}$, 4-$C_7H_{15}$ |
| 10 | 3,5-di-$C_8H_{17}$-phenyl-C(CH$_3$)=CH-CH=O | $H_2N$-phenyl-$OC_5H_{11}$ (para) |
| 11 | 4-$C_4H_9O$-phenyl-CH=CH-CH=O | $H_2N$-phenyl-$C_{13}H_{27}$ (meta) |
| 12 | 3,5-di-$C_3H_7$-phenyl-CH=CH-CH=O | $H_2N$-phenyl-$OC_{15}H_{31}$ (para) |
| 13 | 4-$C_{18}H_{37}$-phenyl-CH=CH-CH=O | $H_2N$-phenyl |
| 14 | 4-$C_6H_{13}$-phenyl-CH=CH-CH=O | $H_2N$-pyridyl-$OC_6H_{13}$ |
| 15 | 4-$C_8H_{17}O$-phenyl-CH=CH-CH=O | $H_2N$-pyridyl-$OC_4H_9$ |
| 16 | 3,5-di-$C_4H_9$-phenyl-CH=CH-CH=O | $H_2N$-pyridyl with $C_4H_9$, $C_4H_9$ |
| 17 | 4-$C_{12}H_{25}O$-phenyl-CH=CH-CH=O | $H_2N$-pyridyl with $H_3C$, phenyl substituents |

TABLE 2-1-continued

| Compound No. | Raw material 1 | Raw material 2 |
|---|---|---|
| 18 | 3-($C_5H_{11}O$)-C$_6$H$_4$-CH=C($C_2H_5$)-CH=O | 5-amino-2-($OC_9H_{19}$)pyridine ($H_2N$-pyridine-$OC_9H_{19}$) |
| 19 | 4-($C_6H_{13}$)-C$_6$H$_4$-CH=CH-CH=O | 5-amino-2-($OC_6H_{13}$)pyridine |

TABLE 2-2

| Compound No. | Raw material 1 | Raw material 2 |
|---|---|---|
| 20 | 4-($C_4H_9$)-C$_6$H$_4$-CH=CH-CH=O | 3-amino-4-($C_4H_9$)pyridine |
| 21 | 4-($C_7H_{15}$)-2-($C_7H_{15}$)-C$_6$H$_3$-CH=CH-CH=O | 3-aminopyridine ($H_2N$-pyridine) |
| 22 | 3-($C_4H_9$)-C$_6$H$_4$-C(CH$_3$)=CH-CH=O | 5-amino-2-($OC_{11}H_{23}$)pyridine |
| 23 | 4-($C_9H_{19}O$)-C$_6$H$_4$-CH=CH-CH=O | 4-amino-2,6-di($OC_4H_9$)pyridine |
| 24 | 3,5-di($C_4H_9O$)-C$_6$H$_3$-CH=CH-CH=O | 4-amino-3-($C_8H_{17}$)pyridine |
| 25 | 4-($C_8H_{17}$)-C$_6$H$_4$-CH=CH-C(CH$_3$)=O | 4-aminopyridine |
| 26 | 4-($C_{14}H_{29}$)-C$_6$H$_4$-C(CH$_3$)=CH-CH=O | 4-aminopyridine |
| 27 | 5-methyl-2-thienyl-CH=CH-CH=O | 4-($OC_6H_{13}$)aniline |

TABLE 2-2-continued

| Compound No. | Raw material 1 | Raw material 2 |
| --- | --- | --- |
| 28 | 3,4-dimethylthiophene-2-CH=CH—CH=O | H$_2$N—C$_6$H$_4$—C$_8$H$_{17}$ (4-) |
| 29 | 5-ethylthiophene-3-CH=CH—C(CH$_3$)=O | H$_2$N—C$_6$H$_4$—OC$_{12}$H$_{25}$ (4-) |
| 30 | 2,5-dimethylthiophene-3-CH=CH—CH=O | 3,5-di-C$_4$H$_9$-C$_6$H$_3$—NH$_2$ |
| 31 | furan-2-CH=CH—CH=O | H$_2$N—C$_6$H$_4$—OC$_6$H$_{13}$ (4-) |
| 32 | 4-methylfuran-2-C(CH$_3$)=CH—C=O | 3-OC$_4$H$_9$-C$_6$H$_4$—NH$_2$ |
| 33 | furan-3-CH=C(C$_2$H$_5$)—CH=O | H$_2$N—C$_6$H$_4$—OC$_9$H$_{19}$ (4-) |
| 34 | furan-3-CH=CH—CH=O | 3,5-di-CH$_3$-4-OC$_5$H$_{11}$-C$_6$H$_2$—NH$_2$ |
| 35 | 5-methyl-1H-pyrrole-2-CH=CH—CH=O | H$_2$N—C$_6$H$_4$—OC$_9$H$_{19}$ (4-) |
| 36 | 4-ethyl-1H-pyrrole-3-CH=CH—CH=O | 3-C$_{10}$H$_{21}$-C$_6$H$_4$—NH$_2$ |
| 37 | 1-methylpyrrole-2-CH=CH—CH=O | H$_2$N—C$_6$H$_4$—OC$_6$H$_{13}$ (4-) |

TABLE 2-2-continued

| Compound No. | Raw material 1 | Raw material 2 |
| --- | --- | --- |
| 38 | 1-methyl-3-methyl-pyrrole-2-yl-CH=CH-C(CH$_3$)=O | 3-$C_8H_{17}$-aniline ($H_2N$-) |

TABLE 2-3

| Compound No. | Raw material 1 | Raw material 2 |
| --- | --- | --- |
| 39 | 1,5-dimethylpyrrol-3-yl-CH=CH-CH=O | 4-$C_{11}H_{23}$-aniline |
| 40 | 1,5-dimethylpyrrol-3-yl-CH=CH-CH=O | 4-$OC_{16}H_{33}$-aniline |
| 41 | 4-$C_8H_{17}O$-C$_6$H$_4$-CH=C(CH$_3$)-CH=O | 2-amino-5-methylthiophene |
| 42 | 3-$C_{10}H_{21}O$-C$_6$H$_4$-CH=CH-CH=O | 2-amino-4-ethylthiophene |
| 43 | 4-$C_{12}H_{25}O$-C$_6$H$_4$-CH=CH-CH=O | 3-amino-5-methylthiophene |
| 44 | 4-$C_6H_{13}O$-C$_6$H$_4$-CH=CH-CH=O | 3-aminofuran |
| 45 | 3-$C_{10}H_{21}O$-C$_6$H$_4$-CH=CH-CH=O | 2-amino-3-methylfuran |
| 46 | 4-$C_9H_{19}$-C$_6$H$_4$-C(CH$_3$)=CH-CH=O | 3-amino-4-ethylfuran |

TABLE 2-3-continued
| Compound No. | Raw material 1 | Raw material 2 |
| --- | --- | --- |
| 47 | 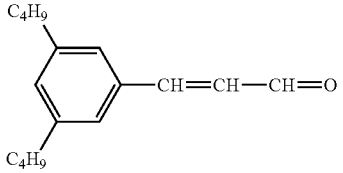 | 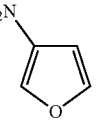 |
| 48 | 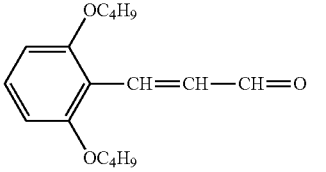 | 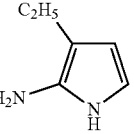 |
| 49 | 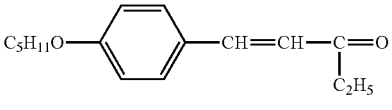 | 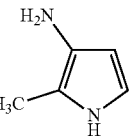 |
| 50 | 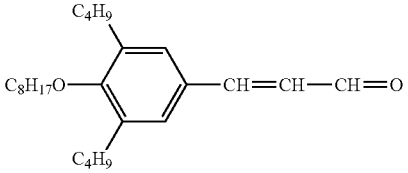 | 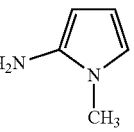 |
| 51 | 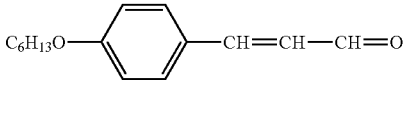 | 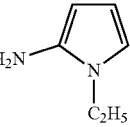 |
| 52 | 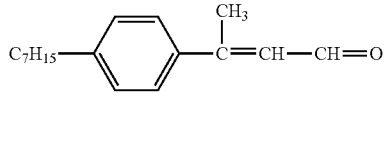 | 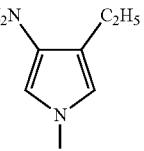 |
| 53 | 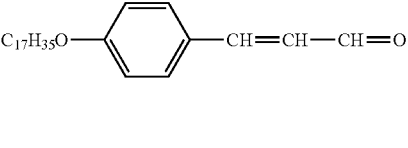 | 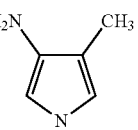 |
| 54 | 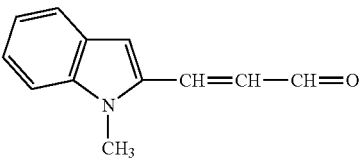 | 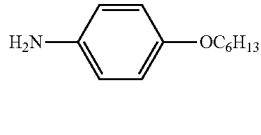 |
| 55 | 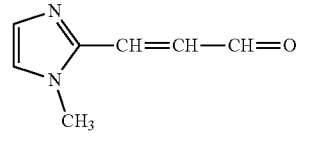 | 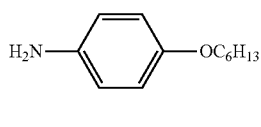 |

TABLE 2-3-continued

| Compound No. | Raw material 1 | Raw material 2 |
|---|---|---|
| 56 | 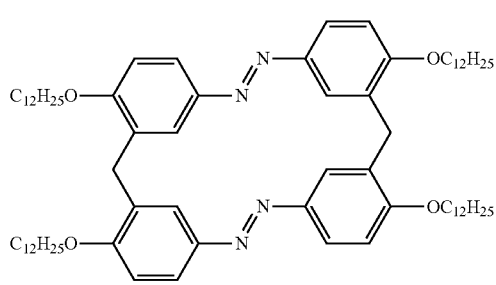 | |
| 57 | | |

(Synthesis of Comparative Compound (Azobenzene Compound) 1)

Comparative Compound (azobenzene compound) 1 represented by the chemical formula (2) shown below was obtained in the same manner as in "(1-2-1) Synthesis of UV Softening Material B" described in paragraphs 0227 to 0237 of JP 2014-191078 A. Production of the comparative compound was confirmed by $^1$H-NMR in the same manner as in Compound No. 5, and it was found that the target Comparative Compound 1 was obtained.

[Chemical Formula 6]

(2)

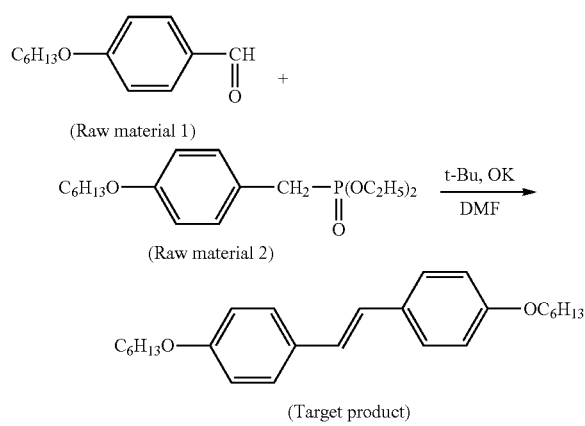

(Synthesis of Comparative Compound (stilbene compound) 2)

[Chemical Formula 7]

To a 50-mL four-necked flask equipped with a condenser and a thermometer, 4-(hexyloxy)benzaldehyde (3.00 g, 14.5 mmol) (raw material 1), diethyl(4-hexyloxy)benzyl)phosphonate (5.25 g, 16.0 mmol) (raw material 2), t-butoxy potassium (2.12 g, 18.9 mmol), and 25 mL of dimethylformamide (DMF) were added and stirred. The resulting mixture was heated and reacted for 3 hours at an internal temperature of 60° C. or more and 75° C. or less.

It was confirmed by thin layer chromatography (TLC) that 4-(hexyloxy)benzaldehyde had disappeared, and after the internal temperature was lowered to room temperature, the reaction liquid was added to 250 mL of water to stop the reaction. The target product was extracted with ethyl acetate and washed with water. The resulting ethyl acetate extract was dried and then concentrated to give crude crystals of Comparative Compound 2. The crude crystals were purified with a silica gel column and concentrated, and the obtained crystals were recrystallized from ethanol to give 4.86 g of Comparative Compound 2 as the target product (yield: 88%). Production of the comparative compound was confirmed by $^1$H-NMR in the same manner as in Compound No. 5, and it was found that the target Comparative Compound 2 was obtained.

[Chemical Formula 8]

(3)

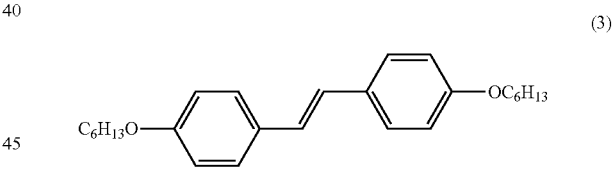

The combinations of substituents (aromatic rings A of $Ar_1$ and $Ar_2$, $R_1$ to $R_{10}$ that are the substituents (a) and (b) of the aromatic rings, X (a hetero group), Y, $Z_1$, and $Z_2$ in the general formula (1)) of Compound Nos. 1 to 57 are as shown in Tables 1-1 to 1-5. The structures of Comparative Compound (azobenzene compound) 1 and Comparative Compound (stilbene compound) 2 are as shown in the chemical formulae (2) and (3), respectively.

<Evaluation Method>
[Photoresponsive Adhesion Test]

The change in adhesiveness of each of the compounds of Examples 1 to 20 and Comparative Examples 1 and 2 (Compound Nos. 2, 7, 10, 14, 18, 22, 25, 27, 29, 31, 34, 35, 39, 41, 46, 49, 51, 53, 54, and 57 and Comparative Compounds 1 and 2) associated with light irradiation was evaluated by a photoresponsive adhesion test described below using the device shown in FIG. 3.

Figure 3:
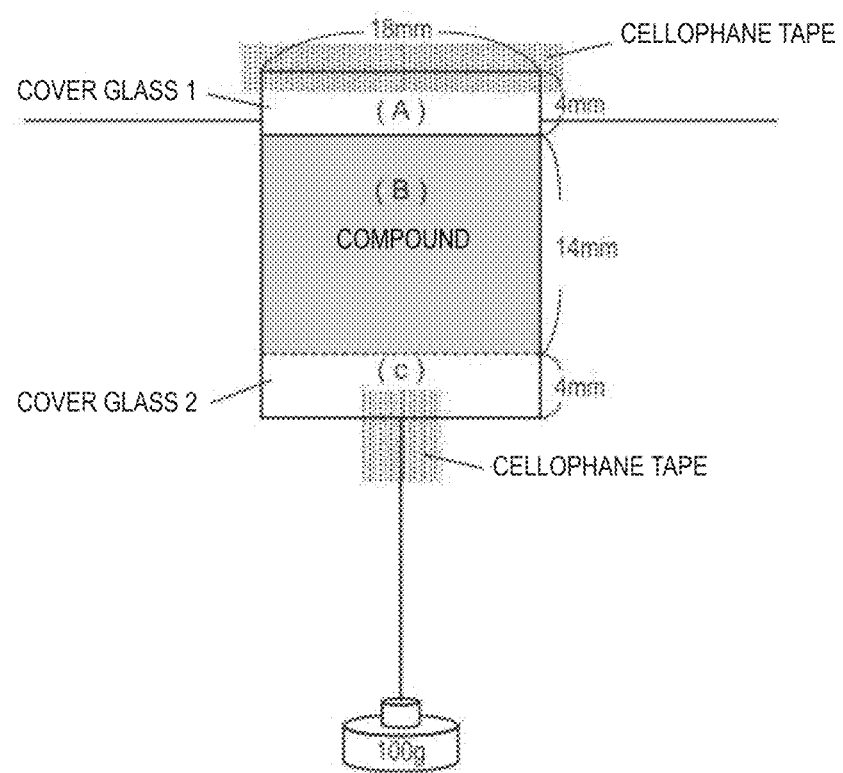
FIG. 3 is a schematic view of a device for measuring a change between fluidity due to light irradiation and non-fluidity (adhesiveness) about photoresponsive compounds synthesized in examples and comparative examples.

As shown in FIG. 3, 2 mg of a compound was placed on a 18-mm square cover glass 1 within a 6-mm radius from the center of the cover glass 1, and a cover glass 2 of the same size was placed on the cover glass 1 at a position shifted by about 4 mm in a direction parallel to the cover glass 1 so as to cover the entire compound. The resulting product was heated to melt the sample (compound), and the cover glass 1 and the cover glass 2 were adhered to each other. Each of the obtained samples was subjected to the following test of non-fluidity→fluidity, and then subjected to the following test of fluidity→non-fluidity.

<Test of Non-Fluidity→Fluidity (Fluidization Test)>

A portion (A) shown in FIG. 3 was fixed to a table with a cellophane tape, and a 30-cm long vinyl string having a weight of 100 g attached thereto was fixed to a portion (C) with a cellophane tape. A portion (B) was irradiated with light having a wavelength of 365 nm at an irradiation amount of 30 J/cm², and whether or not the cover glass 2 was peeled off from the cover glass 1 was observed and determined according to the following evaluation criteria. The obtained results are shown in Tables 3-1 to 3-5 shown below.

Evaluation Criteria for Test of Non-Fluidity→Fluidity (Fluidization Test)
- ○: The cover glass 2 was completely peeled off from the cover glass 1.
- Δ: The cover glass 2 was displaced.
- x: The cover glass 2 did not move.

<Test of Fluidity→Non-Fluidity (Non-Fluidization Test)>

After 5 minutes from the end of light irradiation in the test of non-fluidity→fluidity (during the 5 minutes, the sample was left in a natural environment, that is, at room temperature), a cover glass 3 (having the same size as those of the cover glasses 1 and 2) was placed so as to cover the sample portion (portion (B)) of the cover glass 1 used in the above-mentioned test, and whether or not the cover glasses 1 and 3 were adhered to each other was observed and determined according to the following evaluation criteria. The obtained results are shown in Tables 3-1 to 3-5.

Evaluation Criteria for Test of Fluidity→Non-Fluidity (Non-Fluidization Test)
- ○: Did not adhere (non-fluidized).
- Δ: Partially adhered (the fluidized state was partially maintained).
- x: Adhered (the fluidized state was maintained).

TABLE 3-1

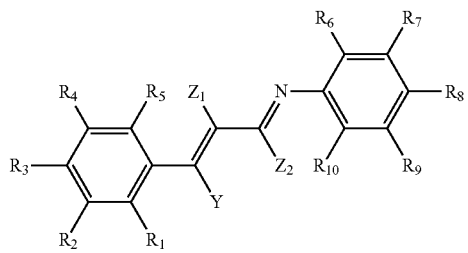

| | Compound No. | $R_1$ | $R_2$ | $R_3$ | $R_4$ | $R_5$ | $R_6$ | $R_7$ | $R_8$ | $R_9$ | $R_{10}$ | Y | $Z_1$ | $Z_2$ | Photoresponsive adhesion test Fluidization test | Non-fluidization test |
|---|---|---|---|---|---|---|---|---|---|---|---|---|---|---|---|---|
| Example 1 | 2 | H | H | $C_6H_{13}$ | H | H | H | H | $OC_6H_{13}$ | H | H | H | H | H | ○ | ○ |
| Example 2 | 7 | H | H | $OC_{11}H_{23}$ | H | H | H | H | $C_{10}H_{21}$ | H | H | H | $C_2H_5$ | H | ○ | ○ |
| Example 3 | 10 | H | $C_8H_{17}$ | H | $C_8H_{17}$ | H | H | H | $OC_5H_{11}$ | H | H | $CH_3$ | H | H | ○ | ○ |

TABLE 3-2

| | Compound No. | A | $R_1$ | $R_2$ | $R_3$ | $R_4$ | $R_5$ | $R_6$ | $R_7$ | $R_8$ | $R_9$ | Y | $Z_1$ | $Z_2$ | Fluidization test | Non-fluidization test |
|---|---|---|---|---|---|---|---|---|---|---|---|---|---|---|---|---|---|
| Example 4 | 14 | $A_1$ | H | H | $C_6H_{13}$ | H | H | H | $OC_6H_{13}$ | H | H | H | H | H | ○ | ○ |
| Example 5 | 18 | $A_2$ | H | $OC_5H_{11}$ | H | H | H | H | $OC_9H_{19}$ | H | H | H | $C_2H_5$ | H | ○ | ○ |
| Example 6 | 22 | | H | $C_4H_9$ | H | H | H | H | $OC_{11}H_{23}$ | H | H | $CH_3$ | H | H | ○ | ○ |
| Example 7 | 25 | $A_3$ | H | H | $C_8H_{17}$ | H | H | H | H | H | H | H | H | $CH_3$ | ○ | ○ |

TABLE 3-3

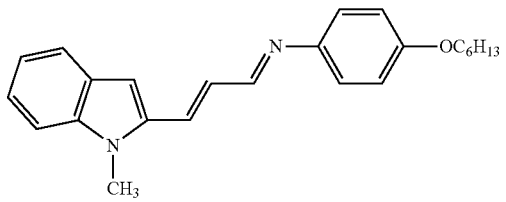

| Compound | | | | | | | | | | | | | | Photoresponsive adhesion test | |
|---|---|---|---|---|---|---|---|---|---|---|---|---|---|---|---|
| | No. | A | X | $R_1$ | $R_2$ | $R_3$ | $R_4$ | $R_5$ | $R_6$ | $R_7$ | $R_8$ | Y | $Z_1$ | $Z_2$ | Fluidization test | Non-fluidization test |
| Example 8 | 27 | $A_1$ | S | $CH_3$ | H | H | H | H | $OC_6H_{13}$ | H | H | H | H | H | ○ | ○ |
| Example 9 | 29 | $A_2$ | | H | $C_2H_5$ | H | H | H | $OC_{12}H_{25}$ | H | H | H | H | $CH_3$ | ○ | ○ |
| Example 10 | 31 | $A_1$ | O | H | H | H | H | H | $OC_6H_{13}$ | H | H | H | H | H | ○ | ○ |
| Example 11 | 34 | $A_2$ | | H | H | H | $CH_3$ | H | $OC_5H_{11}$ | H | $CH_3$ | H | H | H | ○ | ○ |
| Example 12 | 35 | $A_1$ | NH | $CH_3$ | H | H | H | H | $OC_9H_{19}$ | H | H | H | H | H | ○ | ○ |
| Example 13 | 39 | $A_2$ | $NCH_3$ | $CH_3$ | H | H | H | H | $C_{11}H_{23}$ | H | H | H | H | H | ○ | ○ |

TABLE 3-4

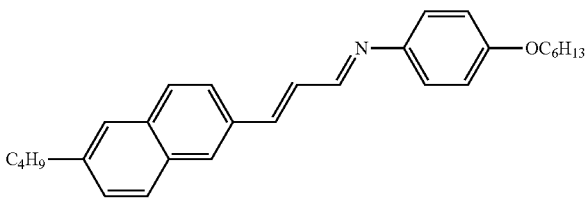

| Compound | | | | | | | | | | | | | | Photoresponsive adhesion test | |
|---|---|---|---|---|---|---|---|---|---|---|---|---|---|---|---|
| | No. | A | X | $R_1$ | $R_2$ | $R_3$ | $R_4$ | $R_5$ | $R_6$ | $R_7$ | $R_8$ | Y | $Z_1$ | $Z_2$ | Fluidization test | Non-fluidization test |
| Example 14 | 41 | $A_1$ | S | $CH_3$ | H | H | H | H | $OC_8H_{17}$ | H | H | H | $CH_3$ | H | ○ | ○ |
| Example 15 | 46 | $A_2$ | O | H | $C_2H_5$ | H | H | H | $C_9H_{19}$ | H | H | $CH_3$ | H | H | ○ | ○ |
| Example 16 | 49 | $A_2$ | NH | $CH_3$ | H | H | H | H | $OC_5H_{11}$ | H | H | H | H | $C_2H_5$ | ○ | ○ |
| Example 17 | 51 | $A_1$ | $NC_2H_5$ | H | H | $CH_3$ | H | H | $OC_6H_{13}$ | H | H | H | H | H | ○ | ○ |
| Example 18 | 53 | $A_2$ | $NCH_3$ | H | $CH_3$ | H | H | H | $OC_{17}H_{35}$ | H | H | H | H | H | ○ | ○ |

TABLE 3-5

| | Compound No. | Structural formula | Photoresponsive adhesion test | |
|---|---|---|---|---|
| | | | Fluidization test | Non-Fluidization test |
| Example 19 | 54 | | ○ | ○ |
| Example 20 | 57 | | ○ | ○ |

TABLE 3-5-continued

| | Compound No. | Structural formula | Photoresponsive adhesion test | |
|---|---|---|---|---|
| | | | Fluidization test | Non-Fluidization test |
| Comparative Example 1 | Comparative Compound 1 | C$_{12}$H$_{25}$O—[phenyl]—N=N—[phenyl]—OC$_{12}$H$_{25}$ linked via CH$_2$ bridges to C$_{12}$H$_{25}$O—[phenyl]—N=N—[phenyl]—OC$_{12}$H$_{25}$ | ○ | × |
| Comparative Example 2 | Comparative Compound 2 | C$_6$H$_{13}$O—[phenyl]—CH=CH—[phenyl]—OC$_6$H$_{13}$ | × | — |

In Table 3-5, as for Comparative Compound 2 of Comparative Example 2, the cover glass 2 did not move in the test of non-fluidity→fluidity (fluidization test). Therefore, in the test of fluidity→non-fluidity (non-fluidization test), it was impossible to place the cover glass 3 so as to cover the sample portion (portion (B)) of the cover glass 1. Accordingly, as for Comparative Compound 2 of Comparative Example 2, since the test of fluidity→non-fluidity (non-fluidization test) was not performed and the evaluation was impossible, the column of evaluation of the "Non-fluidization test" is marked as "-".

[Preparation of Binder Resin]
(Preparation of Styrene Acrylic Resin Particle Dispersion Liquid 1 Containing Styrene Acrylic Resin 1)
(First Stage Polymerization)

To a reaction vessel equipped with a stirrer, a temperature sensor, a condenser, and a nitrogen introduction device, a solution obtained by dissolving 8 parts by mass of sodium dodecyl sulfate in 3000 parts by mass of ion-exchanged water was charged, and the internal temperature was raised to 80° C. with stirring at a stirring speed of 230 rpm under a nitrogen stream. After the temperature rise, a solution obtained by dissolving 10 parts by mass of potassium persulfate in 200 parts by mass of ion-exchanged water was added, the liquid temperature was again adjusted to 80° C., and a polymerizable monomer solution containing 480 parts by mass of styrene, 250 parts by mass of n-butyl acrylate, 68.0 parts by mass of methacrylic acid, and 16.0 parts by mass of n-octyl-3-mercaptopropionate was added dropwise over 1 hour. Then, the mixture was heated and stirred at 80° C. for 2 hours to perform polymerization, thereby preparing a styrene acrylic resin particle dispersion liquid (A) containing styrene acrylic resin particles (1a).

(Second Stage Polymerization)

To a reaction vessel equipped with a stirrer, a temperature sensor, a condenser, and a nitrogen introduction device, a solution obtained by dissolving 7 parts by mass of sodium polyoxyethylene-2-dodecyl ether sulfate in 800 parts by mass of ion-exchanged water was charged. The solution was heated to 98° C., and then 260 parts by mass of the styrene acrylic resin particle dispersion liquid (1A), and a polymerizable monomer solution obtained by dissolving, at 90° C., 245 parts by mass of styrene, 120 parts by mass of n-butyl acrylate, 1.5 parts by mass of n-octyl-3-mercaptopropionate, and 67 parts by mass of paraffin wax "HNP-11" (manufactured by NIPPON SEIRO CO., LTD.) as a release agent were added thereto. Further, the resulting mixture was mixed and dispersed for 1 hour by a mechanical disperser "CLEARMIX" (manufactured by M Technique Co., Ltd.) having a circulation path to prepare a dispersion liquid containing emulsified particles (oil droplets).

Then, an initiator solution obtained by dissolving 6 parts by mass of potassium persulfate in 200 parts by mass of ion-exchanged water was added to the dispersion liquid, and this system was heated and stirred at 82° C. for 1 hour to perform polymerization, thereby preparing a styrene acrylic resin particle dispersion liquid (1B) containing styrene acrylic resin particles (1b).

(Third Stage Polymerization)

A solution obtained by dissolving 11 parts by mass of potassium persulfate in 400 parts by mass of ion-exchanged water was added to the styrene acrylic resin particle dispersion liquid (1B). Then, a polymerizable monomer solution containing 435 parts by mass of styrene, 130 parts by mass of n-butyl acrylate, 33 parts by mass of methacrylic acid, and 8 parts by mass of n-octyl-3-mercaptopropionate was added dropwise over 1 hour at a temperature of 82° C. After completion of the dropwise addition, the mixture was heated and stirred for 2 hours to perform polymerization, and then cooled to 28° C. to obtain a styrene acrylic resin particle dispersion liquid 1 containing a styrene acrylic resin 1.

The particle size of the styrene acrylic resin particles in the styrene acrylic resin particle dispersion liquid 1 was measured by a dynamic light scattering method using "Microtrac UPA-150" (manufactured by NIKKISO CO., LTD.). As a result, the volume-based median diameter was 140 nm. The glass transition temperature Tg of the styrene acrylic resin 1 was measured and found to be 45° C.

(Preparation of Polyester Resin Particle Dispersion Liquid 1 Containing Polyester Resin 1)

To a 10-L four-necked flask equipped with a nitrogen introducing tube, a dehydration tube, a stirrer, and a thermocouple, 524 parts by mass of bisphenol A propylene oxide 2 mol adduct, 105 parts by mass of terephthalic acid, 69 parts by mass of fumaric acid, and 2 parts by mass of tin octylate (an esterification catalyst) were charged, and a polycondensation reaction was performed at a temperature of 230° C. for 8 hours. Further, the polycondensation reaction was continued at 8 kPa for 1 hour, and then the resultant was cooled to 160° C. to obtain a polyester resin 1.

Using "Roundel Mill model RM" (manufactured by TOKUJU CORPORATION), 100 parts by mass of the obtained polyester resin 1 was pulverized. Then, the polyester resin was mixed with 638 parts by mass of a 0.26 mass % aqueous sodium lauryl sulfate solution prepared in advance, and was ultrasonically dispersed at V-LEVEL, 300 μA for 30 minutes using an ultrasonic homogenizer "US-150T" (manufactured by NIHONSEIKI KAISHA LTD.) with stirring to give a polyester resin particle dispersion liquid 1.

The particle size of the polyester resin particles in the polyester resin particle dispersion liquid 1 was measured by a dynamic light scattering method using "Microtrac UPA-150" (manufactured by NIKKISO CO., LTD.). As a result, the volume-based median diameter was 135 nm. The glass transition temperature Tg of the polyester resin 1 was measured and found to be 42° C.

Example 25: Production of Toner 25

(Preparation of Cyan Colorant Particle Dispersion Liquid)

In 1600 parts by mass of pure water, 11.5 parts by mass of sodium n-dodecyl sulfate was dissolved, 25 parts by mass of copper phthalocyanine (C.I. Pigment Blue 15:3) was gradually added thereto, and then the resulting mixture was mixed using "CLEARMIX (registered trademark) W-Motion CLM-0.8 (manufactured by M Technique Co., Ltd.)" to prepare a cyan colorant particle dispersion liquid.

The colorant particles in the cyan colorant particle dispersion liquid had a volume-based median diameter of 110 nm.

(Preparation of Propenimine Compound Particle Dispersion Liquid 5)

At 50° C., 80 parts by mass of dichloromethane and 20 parts by mass of a propenimine compound 5 were mixed and stirred with heating to give a solution containing the propenimine compound 5. To 100 parts by mass of the solution, a mixed liquid of 99.5 parts by mass of distilled water warmed to 50° C. and 0.5 parts by mass of a 20 mass % aqueous sodium dodecylbenzenesulfonate solution was added. Then, the resulting mixture was stirred and emulsified at 16,000 rpm for 20 minutes using a homogenizer (manufactured by Heidolph) equipped with a shaft generator 18F to give a propenimine compound emulsion 5.

The resulting propenimine compound emulsion 5 was charged into a separable flask, and heated and stirred at 40° C. for 90 minutes with nitrogen being fed into the gas phase to remove the organic solvent, thereby obtaining a propenimine compound particle dispersion liquid 5. The propenimine compound particles in the obtained propenimine compound particle dispersion liquid 5 had a mass average particle size of 120 nm. The mass average particle size of the propenimine compound particles in the propenimine compound particle dispersion liquid was measured using an electrophoretic light scattering photometer "ELS-800" (manufactured by Otsuka Electronics Co., Ltd.).

(Aggregation and Fusion)

To a reactor equipped with a stirrer, a temperature sensor, and a condenser, 504 parts by mass in terms of solid content of the styrene acrylic resin particle dispersion liquid 1 prepared as described above, 216 parts by mass in terms of solid content of the propenimine compound particle dispersion liquid 5, 900 parts by mass of ion-exchanged water, and 70 parts by mass in terms of solid content of the cyan colorant particle dispersion liquid were charged. The temperature in the vessel was maintained at 30° C., and a 5 mol/L aqueous sodium hydroxide solution was added to adjust the pH to 10.

Then, an aqueous solution obtained by dissolving 2 parts by mass of magnesium chloride hexahydrate in 1000 parts by mass of ion-exchanged water was added dropwise under stirring over 10 minutes, and then the temperature was started to be raised. The temperature of the system was raised to 70° C. over 60 minutes, and a particle growth reaction was continued with the temperature being maintained at 70° C. In this state, the particle size of associated particles was measured with "Multisizer 3" (manufactured by Beckman Coulter, Inc.), and when the volume-based median diameter (D50) reached 6.5 μm, an aqueous solution obtained by dissolving 190 parts by mass of sodium chloride in 760 parts by mass of ion-exchanged water was added to stop the particle growth. The resulting mixture was stirred at 70° C. for 1 hour, then the temperature was further raised, and the mixture was heated and stirred at 75° C. to advance fusion of the particles. Then, the mixture was cooled to 30° C. to give a dispersion liquid of toner particles.

The dispersion liquid of toner particles obtained as described above was subjected to solid-liquid separation with a centrifuge to form a wet cake of the toner particles. The wet cake was washed with ion-exchanged water at 35° C. in the centrifuge until the filtrate had an electric conductivity of 5 μS/cm, then transferred to "Flash Jet Dryer (manufactured by SEISHIN ENTERPRISE Co., Ltd.)", and dried until the water content reached 0.5 mass %, thereby producing Toner 25.

Examples 21 to 24 and 26 to 77: Production of Toners 21 to 24 and 26 to 77

Toners 21 to 24 and 26 to 77 were produced in the same manner as in the production of Toner 25 except that the type of the propenimine compound was changed as shown in Tables 4-1 and 4-2.

Examples 78 to 83: Production of Toners 78 to 83

Toners 78 to 83 were produced in the same manner as in the production of Toner 25 except that the amount of addition (ratio) of the propenimine compound was changed as shown in Table 4-2.

Examples 84 to 86: Production of Toners 84 to 86

Toners 84 to 86 were produced in the same manner as in the production of Toner 25 except that the styrene acrylic resin particle dispersion liquid 1 was changed to the polyester resin particle dispersion liquid 1, and that the amount of addition (ratio) of the propenimine compound was changed as shown in Table 4-2.

In Examples 87 and 88, Toner 25 was used.

Comparative Examples 3 and 4: Production of Toners 87 and 88

Toners 87 and 88 were produced in the same manner as in the production of Toner 25 except that Comparative Compound (azobenzene compound) 1 and Comparative Compound (stilbene compound) 2 shown in Table 4-2 were respectively used instead of the propenimine compound.

[Production of Developers 21 to 88]

In a 20-mL glass container, 9.5 g of an iron powder having a volume-based median diameter of 70 μm and 0.5 g of a toner were charged, and the contents were shaken 200 times per minute at a shaking angle of 45 degrees with a 50-cm arm for 20 minutes to produce Developers 21 to 88.

<Image Formation and Evaluation>

[Image Formation]

Using each of the obtained developers, a toner image was formed on plain paper as a recording medium to produce a printed matter. Specifically, a developer was disposed while being slid by a magnetic force between a pair of parallel plate (aluminum) electrodes having a developer on one side and gloss coated paper (basis weight: 128 g/m$^2$) on the other side. A toner was developed at a gap between electrodes of 0.5 mm under conditions of a DC bias and an AC bias so that a toner adhesion amount would be 4 g/m$^2$, and a toner image was formed on the surface of the plain paper and fixed by a fixing device to produce a printed matter.

[Evaluation: Fixability Test]

A 1-cm square image of the printed matter was rubbed 10 times with "JK Wiper (registered trademark)" (manufactured by NIPPON PAPER CRECIA CO., LTD.) under a pressure of 50 kPa, and the fixing ratio of the image was evaluated. A fixing ratio of 50% or more is regarded as pass. The obtained evaluation results of the fixability test are shown in Tables 4-1 and 4-2 shown below. Herein, the image fixing ratio is a numerical value obtained by measuring the densities of the image after printing and the image after rubbing with a reflection densitometer "RD-918" (manufactured by SAKATA INX ENG. CO., LTD.), and dividing the reflection density of the solid image after rubbing by the reflection density of the solid image after printing, and is expressed in percentage.

As for the fixing device, the following three types of devices formed by appropriately modifying the device illustrated in FIG. 2 were used.

Fixing device No. 1: In FIG. 2, the pressure-bonding unit 9 is omitted, the irradiation unit 40 emits ultraviolet light having a wavelength of 365 nm (light source: an LED light source having an emission wavelength of 365 nm±10 nm), and the irradiation amount is 10 J/cm$^2$.

Fixing device No. 2: In FIG. 2, the pressure-bonding unit 9 is provided, the pressurizing member 91 has a temperature of 20° C. (without heating), and the pressure at the time of pressurization is 0.2 MPa. The light source and the irradiation amount of the irradiation unit 40 are similar to those of the fixing device No. 1.

Fixing device No. 3: In FIG. 2, the pressure-bonding unit 9 is provided, the pressurizing member 91 has a temperature of 80° C. (with heating), and the pressure at the time of pressurization is 0.2 MPa. The light source and the irradiation amount of the irradiation unit 40 are similar to those of the fixing device No. 1.

[Color Reproducibility Evaluation]

The images of examples obtained as described above were evaluated for color reproducibility based on visual inspection by 10 panelists according to the following evaluation criteria. Specifically, as comparative samples, toners obtained by removing only the propenimine compound from the toners described in the examples were produced, and toners obtained by removing only Comparative Compound (azobenzene compound) 1 and Comparative Compound (stilbene compound) 2 from Toners 91 and 92 described in Comparative Examples 3 and 4, respectively, were produced. Using these toners, development was performed in the same manner as in [Image forming method], and the resulting images were fixed by the following fixing device No. 4 formed by appropriately modifying the device illustrated in FIG. 2.

Fixing device No. 4: In FIG. 2, the pressure-bonding unit 9 is provided, the pressurizing member 91 has a temperature of 150° C. (with heating), and the pressure at the time of pressurization is 0.2 MPa. Meanwhile, the fixing device No. 4 had a device configuration in which the irradiation unit 40 in FIG. 2 is omitted and light irradiation is not performed.

The 10 panelists were shown the comparative samples and the example samples in order, and asked if the colors of the two images were clearly different. The determination results according to the following evaluation criteria for color reproducibility are shown in Tables 4-1 and 4-2 shown below.

Evaluation Criteria for Color Reproducibility

⊚: 2 or less panelists answered that the images had clearly different colors.

○: 3 or more and 4 or less panelists answered that the images had clearly different colors.

Δ: 5 or more and 7 or less panelists answered that the images had clearly different colors.

×: 8 or more panelists answered that the images had clearly different colors.

The compounds, the composition of the toners (developers), the type of the fixing devices, and the evaluation results (fixing ratio (%) and color reproducibility) are shown in Tables 4-1 and 4-2 shown below.

TABLE 4-1

| | Compound No. | Ratio (mass %) | Binder resin | Colorant | Toner (developer) No. | Fixing device No. | Evaluation results Fixing ratio (%) | Color reproducibility |
|---|---|---|---|---|---|---|---|---|
| Example 21 | 1 | 30 | Styrene acrylic resin | Cyan | 21 | 1 | 75 | ⊚ |
| Example 22 | 2 | 30 | Styrene acrylic resin | Cyan | 22 | 1 | 90 | ⊚ |
| Example 23 | 3 | 30 | Styrene acrylic resin | Cyan | 23 | 1 | 75 | ⊚ |
| Example 24 | 4 | 30 | Styrene acrylic resin | Cyan | 24 | 1 | 80 | ⊚ |
| Example 25 | 5 | 30 | Styrene acrylic resin | Cyan | 25 | 1 | 90 | ⊚ |
| Example 26 | 6 | 30 | Styrene acrylic resin | Cyan | 26 | 1 | 89 | ⊚ |
| Example 27 | 7 | 30 | Styrene acrylic resin | Cyan | 27 | 1 | 72 | ⊚ |
| Example 28 | 8 | 30 | Styrene acrylic resin | Cyan | 28 | 1 | 82 | ⊚ |
| Example 29 | 9 | 30 | Styrene acrylic resin | Cyan | 29 | 1 | 81 | ⊚ |
| Example 30 | 10 | 30 | Styrene acrylic resin | Cyan | 30 | 1 | 78 | ⊚ |
| Example 31 | 11 | 30 | Styrene acrylic resin | Cyan | 31 | 1 | 78 | ⊚ |
| Example 32 | 12 | 30 | Styrene acrylic resin | Cyan | 32 | 1 | 75 | ⊚ |

TABLE 4-1-continued

|  | Compound No. | Ratio (mass %) | Binder resin | Colorant | Toner (developer) No. | Fixing device No. | Fixing ratio (%) | Color reproducibility |
|---|---|---|---|---|---|---|---|---|
| Example 33 | 13 | 30 | Styrene acrylic resin | Cyan | 33 | 1 | 73 | ⊙ |
| Example 34 | 14 | 30 | Styrene acrylic resin | Cyan | 34 | 1 | 83 | ⊙ |
| Example 35 | 15 | 30 | Styrene acrylic resin | Cyan | 35 | 1 | 85 | ⊙ |
| Example 36 | 16 | 30 | Styrene acrylic resin | Cyan | 36 | 1 | 75 | ⊙ |
| Example 37 | 17 | 30 | Styrene acrylic resin | Cyan | 37 | 1 | 72 | ◯ |
| Example 38 | 18 | 30 | Styrene acrylic resin | Cyan | 38 | 1 | 70 | ⊙ |
| Example 39 | 19 | 30 | Styrene acrylic resin | Cyan | 39 | 1 | 83 | ⊙ |
| Example 40 | 20 | 30 | Styrene acrylic resin | Cyan | 40 | 1 | 73 | ⊙ |
| Example 41 | 21 | 30 | Styrene acrylic resin | Cyan | 41 | 1 | 72 | ⊙ |
| Example 42 | 22 | 30 | Styrene acrylic resin | Cyan | 42 | 1 | 78 | ⊙ |
| Example 43 | 23 | 30 | Styrene acrylic resin | Cyan | 43 | 1 | 78 | ⊙ |
| Example 44 | 24 | 30 | Styrene acrylic resin | Cyan | 44 | 1 | 71 | ⊙ |
| Example 45 | 25 | 30 | Styrene acrylic resin | Cyan | 45 | 1 | 68 | ⊙ |
| Example 46 | 26 | 30 | Styrene acrylic resin | Cyan | 46 | 1 | 73 | ⊙ |
| Example 47 | 27 | 30 | Styrene acrylic resin | Cyan | 47 | 1 | 82 | ⊙ |
| Example 48 | 28 | 30 | Styrene acrylic resin | Cyan | 48 | 1 | 77 | ⊙ |
| Example 49 | 29 | 30 | Styrene acrylic resin | Cyan | 49 | 1 | 80 | ⊙ |
| Example 50 | 30 | 30 | Styrene acrylic resin | Cyan | 50 | 1 | 72 | ⊙ |
| Example 51 | 31 | 30 | Styrene acrylic resin | Cyan | 51 | 1 | 89 | ⊙ |
| Example 52 | 32 | 30 | Styrene acrylic resin | Cyan | 52 | 1 | 73 | ⊙ |
| Example 53 | 33 | 30 | Styrene acrylic resin | Cyan | 53 | 1 | 70 | ⊙ |
| Example 54 | 34 | 30 | Styrene acrylic resin | Cyan | 54 | 1 | 75 | ⊙ |
| Example 55 | 35 | 30 | Styrene acrylic resin | Cyan | 55 | 1 | 79 | ⊙ |
| Example 56 | 36 | 30 | Styrene acrylic resin | Cyan | 56 | 1 | 68 | ⊙ |
| Example 57 | 37 | 30 | Styrene acrylic resin | Cyan | 57 | 1 | 88 | ⊙ |
| Example 58 | 38 | 30 | Styrene acrylic resin | Cyan | 58 | 1 | 75 | ⊙ |
| Example 59 | 39 | 30 | Styrene acrylic resin | Cyan | 59 | 1 | 79 | ⊙ |
| Example 60 | 40 | 30 | Styrene acrylic resin | Cyan | 60 | 1 | 79 | ⊙ |

TABLE 4-2

|  | Compound No. | Ratio (mass %) | Binder resin | Colorant | Toner (developer) No. | Fixing device No. | Fixing ratio (%) | Color reproducibility |
|---|---|---|---|---|---|---|---|---|
| Example 61 | 41 | 30 | Styrene acrylic resin | Cyan | 61 | 1 | 70 | ⊙ |
| Example 62 | 42 | 30 | Styrene acrylic resin | Cyan | 62 | 1 | 72 | ⊙ |
| Example 63 | 43 | 30 | Styrene acrylic resin | Cyan | 63 | 1 | 77 | ⊙ |
| Example 64 | 44 | 30 | Styrene acrylic resin | Cyan | 64 | 1 | 85 | ⊙ |
| Example 65 | 45 | 30 | Styrene acrylic resin | Cyan | 65 | 1 | 73 | ⊙ |
| Example 66 | 46 | 30 | Styrene acrylic resin | Cyan | 66 | 1 | 70 | ⊙ |
| Example 67 | 47 | 30 | Styrene acrylic resin | Cyan | 67 | 1 | 74 | ⊙ |
| Example 68 | 48 | 30 | Styrene acrylic resin | Cyan | 68 | 1 | 75 | ⊙ |
| Example 69 | 49 | 30 | Styrene acrylic resin | Cyan | 69 | 1 | 69 | ⊙ |
| Example 70 | 50 | 30 | Styrene acrylic resin | Cyan | 70 | 1 | 66 | ⊙ |
| Example 71 | 51 | 30 | Styrene acrylic resin | Cyan | 71 | 1 | 73 | ⊙ |
| Example 72 | 52 | 30 | Styrene acrylic resin | Cyan | 72 | 1 | 68 | ⊙ |
| Example 73 | 53 | 30 | Styrene acrylic resin | Cyan | 73 | 1 | 70 | ◯ |
| Example 74 | 54 | 30 | Styrene acrylic resin | Cyan | 74 | 1 | 72 | ◯ |
| Example 75 | 55 | 30 | Styrene acrylic resin | Cyan | 75 | 1 | 68 | ⊙ |
| Example 76 | 56 | 30 | Styrene acrylic resin | Cyan | 76 | 1 | 62 | ⊙ |
| Example 77 | 57 | 30 | Styrene acrylic resin | Cyan | 77 | 1 | 61 | ◯ |
| Example 78 | 5 | 10 | Styrene acrylic resin | Cyan | 78 | 1 | 73 | ⊙ |
| Example 79 | 5 | 20 | Styrene acrylic resin | Cyan | 79 | 1 | 85 | ⊙ |
| Example 80 | 5 | 50 | Styrene acrylic resin | Cyan | 80 | 1 | 80 | ⊙ |
| Example 81 | 5 | 70 | Styrene acrylic resin | Cyan | 81 | 1 | 69 | ⊙ |
| Example 82 | 5 | 90 | Styrene acrylic resin | Cyan | 82 | 1 | 62 | ⊙ |
| Example 83 | 5 | 100 | — | Cyan | 83 | 1 | 59 | ⊙ |
| Example 84 | 5 | 10 | Polyester resin | Cyan | 84 | 1 | 70 | ⊙ |
| Example 85 | 5 | 30 | Polyester resin | Cyan | 85 | 1 | 91 | ⊙ |
| Example 86 | 5 | 50 | Polyester resin | Cyan | 86 | 1 | 82 | ⊙ |
| Example 87 | 5 | 30 | Styrene acrylic resin | Cyan | 25 | 2 | 90 | ⊙ |
| Example 88 | 5 | 30 | Styrene acrylic resin | Cyan | 25 | 3 | 93 | ⊙ |
| Comparative Example 3 | Comparative Compound 1 | 30 | Styrene acrylic resin | Cyan | 87 | 1 | 45 | X |
| Comparative Example 4 | Comparative Compound 2 | 30 | Styrene acrylic resin | Cyan | 88 | 1 | 35 | ◯ |

The "Compound No." in Tables 4-1 and 4-2 refers to "Compound No." of the propenimine compounds of the general formula (1) shown in Tables 1-1 to 1-5. Comparative Compounds 1 and 2 in Table 4-2 refer to Comparative Compound (azobenzene compound) 1 and Comparative Compound (stilbene compound) 2 represented by the chemical formulae (2) and (3), respectively. The "Ratio" in Tables 4-1 and 4-2 indicates the ratio (unit: mass %) of the propenimine compound based on the total amount of the propenimine compound and the binder resin in the toner. The "Ratio" as for Comparative Examples 3 and 4 in Table 4-2 indicates the ratio (unit: mass %) of the azobenzene compound or the stilbene compound, respectively, based on the total amount of the azobenzene compound or the stilbene compound and the binder resin in the toner.

As is apparent from Tables 4-1 and 4-2, the toners of Examples 21 to 88 exhibited a high fixing ratio and excellent color reproducibility.

This is because conjugation of the azobenzene compound and the stilbene compound respectively contained in the toners of Comparative Examples 3 and 4 is increased due to introduction of a benzene ring, and therefore the azobenzene compound and the stilbene compound have strong absorption due to $\pi$-$\pi^*$ transition in a long wavelength region. Therefore, it is considered that even though the azobenzene compound and the stilbene compound were mixed with the colorant, desired color reproduction was impossible because colors possessed by the azobenzene compound and the stilbene compound were exhibited. Meanwhile, it was found that since the toners of examples of the present invention contained the propenimine compound represented by the general formula (1) having a —C=C—C=N— structure, the toners are capable of weakening the strong absorption due to $\pi$-$\pi^*$ transition in a long wavelength region and preventing strong yellow color development, so that the toners have excellent color reproducibility when being mixed with a colorant.

In addition, the aromatic rings of the propenimine compound contained in the toners of the examples of the present invention are substituted with an alkyl group and/or an alkoxy group (see Tables 1-1 to 1-5). Since these alkyl groups and alkoxy groups have thermal mobility, the propenimine compound contained in the toners of the examples of the present invention forms a specific crystal structure in which, in a periodic structure dominated by the $\pi$-$\pi$ interaction, a structure isotropically disturbed by thermal motion of the alkyl groups or the alkoxy groups coexists. Therefore, when the cis-trans isomerization reaction locally proceeds and the $\pi$-$\pi$ interaction of the propenimine moiety is reduced, isotropic melting occurs in a chain manner in the entire system. Therefore, it is considered that trans-cis isomerization is more likely to proceed, and fluidization of the toner due to light irradiation is more likely to occur.

Further, it is considered that the rate of the Z→E reaction was controlled in the toners of the examples of the present invention since the toners contained the propenimine compound in which a vinylene group having a high energy barrier and a low rate of the Z→E reaction is connected to an azomethine group having a low energy barrier. That is, it is considered that when the propenimine compound was changed (fluidized) from a trans isomer (E) to a cis isomer (Z) by light irradiation, the rate of the Z→E reaction (non-fluidization reaction), which is a reverse reaction, was controlled so as not to be too fast, and the softened state necessary for fixing was maintained.

From these facts, it is considered that introduction of the propenimine compound, which induces reversible fluidization and non-fluidization phenomena associated with to photoisomerization while being colorless, into a toner realized a high fixing ratio by light irradiation and excellent color reproducibility.

Meanwhile, it was found that the toner of Comparative Example 3 had a fixing ratio lower than 50% and poor color reproducibility. The toner of Comparative Example 4 was found to have a fixing ratio significantly lower than 50%. Since the light irradiation conditions (light source and irradiation amount of ultraviolet light) by the irradiation unit 40 used in the fixability test were the same throughout Examples 21 to 88 and Comparative Examples 1 and 2, it can be said that the toners of the examples, as compared with the toners of the comparative examples, sufficiently exhibited the effect by the propenimine compound that is reversibly fluidized and non-fluidized by light irradiation and is not significantly colored. That is, it was found that the toners of the examples, as compared with the toners of the comparative examples, have no influence on desired color reproduction when being mixed with the colorant, have a remarkably improved softening rate (both the rate of fluidization (E→Z reaction) and the rate of non-fluidization (Z→E reaction) that is a reverse reaction), and have good fixability. In addition, it was also found that use of the toner provides an image forming method excellent in color reproducibility and fixability of an image.

As a result of comparison of the fixing devices, it was found that light irradiation alone by the fixing device No. 1, in which light is emitted by the irradiation unit 40 under the same conditions and no pressurizing member is used, provides sufficient fixability. In addition, it was found that the fixability is further improved by using the fixing device No. 2 that pressurizes the image by the pressurizing member and the fixing device No. 3 that pressurizes and heats the image by the pressurizing member (comparison among Examples 25, 87, and 88). Further, conventional toners are difficult to fix only by pressurization. In the case of the light-melting toner of the present invention, the fixability is improved as compared with the case of heating and pressurizing a conventional toner, and the light irradiation energy applied at the time of fixing is smaller than the conventional fixing energy (energy of heating and pressurization). From this, it is understood that the fixing device No. 1 that does not pressurize or heat the image is most preferred from the viewpoint of simplification and size reduction of the configuration, energy saving, prevention of global warming ($CO_2$ reduction), and the like.

As for the relationship between the type of the binder resin and the "ratio" of the propenimine compound in the toner in the examples, it is understood that in the case of the polyester resin, the "ratio" of the propenimine compound is preferably in the range of 10 mass % or more and less than 70 mass %, more preferably in the range of 20 mass % or more and 60 mass % or less, and the "ratio" of the propenimine compound is still more preferably in the range of 30 mass % or more and 50 mass % or less. It is also understood that in the case of the styrene acrylic resin, the "ratio" of the propenimine compound is preferably in the range of 10 mass % or more and 70 mass % or less, more preferably in the range of 20 mass % or more and 60 mass % or less, and still more preferably in the range of 20 mass % or more and 50 mass % or less. That is, when the ratio of the propenimine compound in the toner is within the above-mentioned range, high fixability is obtained. From the above-mentioned range of the "ratio", it can be said that both the styrene acrylic resin and the polyester resin are preferred as the binder resin.

Among Examples 25 to 77 in which the propenimine compound in the toner was varied, suitable compounds are Compound Nos. 2, 3, 5, and 10 from a wide range of viewpoints aside from the fixing ratio and color reproducibility, such as ease of production, manufacturing cost, yield, storability, handleability, durability, and influence on toner performance other than the fixing ratio and color reproducibility. Further, from the viewpoint of compatibility, suitable examples are Examples 22, 25, 35, and 57. From the viewpoint of toner fixability alone, Compound Nos. 2, 5, 6, 15, 31, 37, and 44 (Examples 22, 25, 26, 35, 51, 57, and 64) are preferred.

Although embodiments of the present invention have been described and illustrated in detail, the disclosed embodiments are made for purposes of illustration and example only and not limitation. The scope of the present invention should be interpreted by terms of the appended claims.

The entire disclosure of Japanese Patent Application No. 2020-145011, filed on Aug. 28, 2020, is incorporated herein by reference in its entirety.

What is claimed is:

1. A compound that is fluidized by light irradiation and reversibly non-fluidized and is represented by the following general formula (1):

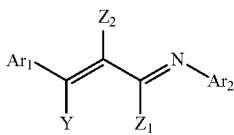

General formula (1)

wherein,
$Ar_1$ and $Ar_2$ each independently represent an aromatic hydrocarbon group optionally having a substituent (a) or an aromatic heterocyclic group optionally having a substituent (b), provided that at least one of $Ar_1$ or $Ar_2$ represents the aromatic heterocyclic group optionally having the substituent (b), and
Y, $Z_1$, and $Z_2$ each independently represent a hydrogen atom or a lower alkyl group, and
the compound comprises an alkoxy group having 1 to 18 carbon atoms as the substituent (a) or (b).

2. The compound according to claim 1, wherein the substituents (a) and (b) are each independently an alkyl group having 1 to 18 carbon atoms, an alkoxy group having 1 to 18 carbon atoms, an aromatic hydrocarbon group optionally having a substituent (c), or an aromatic heterocyclic group optionally having a substituent (d), provided that the substituent (a) or (b) is the alkoxy group having 1 to 18 carbon atoms.

3. The compound according to claim 2, wherein the substituents (c) and (d) are each independently an alkyl group having 1 to 8 carbon atoms or an alkoxy group having 1 to 8 carbon atoms.

4. The compound according to claim 1, wherein the lower alkyl group is an alkyl group having 1 to 2 carbon atoms.

5. A toner comprising a compound that is fluidized by light irradiation and reversibly non-fluidized and is represented by the following general formula (1):

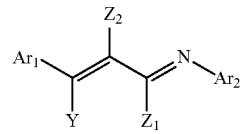

General formula (1)

wherein,
$Ar_1$ and $Ar_2$ each independently represent an aromatic hydrocarbon group optionally having a substituent (a) or an aromatic heterocyclic group optionally having a substituent (b), and
Y, $Z_1$, and $Z_2$ each independently represent a hydrogen atom or a lower alkyl group.

6. The toner according to claim 5, further comprising a binder resin.

7. The toner according to claim 6, wherein the binder resin includes at least one selected from the group consisting of a styrene-acrylic resin and a polyester resin.

8. The toner according to claim 5, further comprising a colorant.

9. An image forming method comprising:
forming an image on a recording medium using a toner containing the compound according to claim 1;
irradiating the image formed on the recording medium with light in a wavelength region of 280 nm or more and 420 nm or less; and
fixing the image on the recording medium.

10. The image forming method according to claim 9, wherein the fixing of the image on the recording medium includes pressurizing, with a pressurizing member, the recording medium on which the image is formed.

11. The image forming method according to claim 10, wherein the pressurizing member has a temperature of 30° C. or more and 100° C. or less.

12. A photoresponsive adhesive comprising the compound according to claim 1.

13. An optical switching material comprising the compound according to claim 1.

14. The compound according to claim 1, wherein the aromatic heterocyclic group is selected from the group consisting of a pyridine ring group, a furan ring group, a thiophene ring group, a pyrrole ring group, an indole ring group, an imidazole ring group, and a thiazole ring group.

* * * * *